US010722429B2

(12) United States Patent
Shibasaki

(10) Patent No.: US 10,722,429 B2
(45) Date of Patent: Jul. 28, 2020

(54) LIQUID MEDICATION DISPENSING MACHINE

(71) Applicant: TAKAZONO TECHNOLOGY INCORPORATED, Hirakata-shi, Osaka (JP)

(72) Inventor: Tetsuya Shibasaki, Hirakata (JP)

(73) Assignee: TAKAZONO TECHNOLOGY INCORPORATED, Hirakata-shi, Osaka (JP)

( * ) Notice: Subject to any disclaimer, the term of this patent is extended or adjusted under 35 U.S.C. 154(b) by 272 days.

(21) Appl. No.: 15/632,914

(22) Filed: Jun. 26, 2017

(65) Prior Publication Data

US 2017/0290743 A1 Oct. 12, 2017

Related U.S. Application Data

(62) Division of application No. 13/993,499, filed as application No. PCT/JP2011/078524 on Dec. 9, 2011, now abandoned.

(30) Foreign Application Priority Data

Dec. 28, 2010 (JP) .................................. 2010-292637

(51) Int. Cl.
| | |
|---|---|
| *B01F 3/08* | (2006.01) |
| *A61J 1/20* | (2006.01) |
| *B65B 3/00* | (2006.01) |
| *B01F 9/00* | (2006.01) |
| *B01F 9/10* | (2006.01) |
| *B01F 15/04* | (2006.01) |
| *G07F 13/10* | (2006.01) |
| *G07F 17/00* | (2006.01) |
| *B01F 13/10* | (2006.01) |
| *A61J 1/00* | (2006.01) |
| *G06F 19/00* | (2018.01) |
| *B01F 15/00* | (2006.01) |
| *A61J 3/00* | (2006.01) |

(52) U.S. Cl.
CPC .............. *A61J 1/2089* (2013.01); *A61J 1/00* (2013.01); *B01F 3/08* (2013.01); *B01F 9/0014* (2013.01); *B01F 9/10* (2013.01); *B01F 13/1055* (2013.01); *B01F 13/1066* (2013.01); *B01F 15/0445* (2013.01); *B65B 3/003* (2013.01); *G06F 19/3462* (2013.01); *G07F 13/10* (2013.01); *G07F 17/0092* (2013.01); *A61J 3/002* (2013.01); *B01F 2015/00636* (2013.01); *B01F 2215/0032* (2013.01)

(58) Field of Classification Search
CPC ........................................................ B01F 3/0803
USPC ............................................ 366/154.1, 155.1
See application file for complete search history.

(56) References Cited

U.S. PATENT DOCUMENTS

| | | | |
|---|---|---|---|
| 2,423,969 | A | 7/1947 | Foltz |
| 3,208,823 | A | 9/1965 | Baker et al. |
| 5,192,130 | A | 3/1993 | Endo et al. |
| 5,206,479 | A | 4/1993 | Zakaria et al. |
| 5,272,092 | A | 12/1993 | Hamasaki et al. |
| 6,357,907 | B1 | 3/2002 | Cleveland et al. |
| 2004/0267228 | A1 | 12/2004 | Hattori et al. |
| 2008/0212401 | A1* | 9/2008 | Alessandro ......... B01F 13/1058 366/152.1 |

FOREIGN PATENT DOCUMENTS

| | | |
|---|---|---|
| CN | 1553790 A | 12/2004 |
| EP | 2208679 A1 | 7/2010 |
| JP | 59-71755 A | 4/1984 |
| JP | 1-244759 A | 9/1989 |
| JP | 2000-217906 A | 8/2000 |
| JP | 2003-248009 A | 9/2003 |
| JP | 2007-014464 A | 1/2007 |
| JP | 2007-14618 A | 1/2007 |
| JP | 2007-21087 A | 2/2007 |
| JP | 2007-40843 A | 2/2007 |
| JP | 2007-108937 A | 4/2007 |
| JP | 2007-202625 A | 8/2007 |

(Continued)

OTHER PUBLICATIONS

Office Action dated Nov. 21, 2017, issued in counterpart Japanese Application No. 2016-139248, with English translation. (5 pages).
International Search Report dated Feb. 7, 2012, issued in corresponding application No. PCT/JP2011/078524.
Office Action dated Mar. 27, 2014, issued in Chinese Patent Application No. 201180063570.X with English Translation (14 pages).
Office Action dated Feb. 3, 2015, issued in corresponding Japanese Patent Application No. 2010-292637, with English Translation (6 pages).

(Continued)

*Primary Examiner* — David L Sorkin
(74) *Attorney, Agent, or Firm* — Westerman, Hattori, Daniels & Adrian, LLP

(57) ABSTRACT

Provided is a liquid medication dispensing machine that can shorten the time to supply a liquid medication to a prescription bottle. The liquid medication dispensing machine is a liquid medication dispensing machine supplying a liquid medication from a liquid medication bottle containing the liquid medication to a prescription bottle, including a liquid medication stirring unit that stirs the liquid medication in the liquid medication bottle, a bottle holding unit that holds a plurality of liquid medication bottles including a first bottle containing a liquid medication G and a second bottle containing a liquid medication B, and a control unit that controls operation of the liquid medication dispensing machine. The control unit operates the liquid medication stirring unit to stir liquid medication B while liquid medication G is supplied from the first bottle to the prescription bottle.

4 Claims, 21 Drawing Sheets

(56) References Cited

FOREIGN PATENT DOCUMENTS

| | | |
|---|---|---|
| JP | 2007-244632 A | 9/2007 |
| JP | 2007-319382 A | 12/2007 |
| JP | 2008-079695 A | 4/2008 |
| JP | 2008-081135 A | 4/2008 |
| JP | 2009-112673 A | 5/2009 |
| JP | 2009-113851 A | 5/2009 |
| WO | 2010/110303 A1 | 9/2010 |

OTHER PUBLICATIONS

Office Action dated Mar. 17, 2017, issued in Korean Patent Application No. 10-2013-7019370, with English translation. (6 pages).
Office Action dated May 9, 2017, issued in counterpart Japanese application No. 2016-139248, with English translation. (5 pages).
Office Action dated Oct. 29, 2019, issued in counterpart Japanese Application No. 2018-156425, with English translation. (5 pages).

* cited by examiner

FIG.11

| TYPE OF LIQUID MEDICATION | CURRENT POSITION | MOVING TIME TO DISPENSING POSITION (s) |
|---|---|---|
| A | 1 | 0 |
| B | 2 | 3 |
| C | 3 | 6 |
| D | 4 | 9 |
| E | 5 | 12 |
| F | 6 | 9 |
| G | 7 | 6 |
| H | 8 | 3 |

FIG.12

| TYPE OF LIQUID MEDICATION | REQUIRED STIRRING TIME (s) |
|---|---|
| A | |
| B | 10 |
| C | |
| D | |
| E | 10 |
| F | |
| G | |
| H | |

| NUMBER | TYPE OF LIQUID MEDICATION | DISPENSING QUANTITY (ml) |
|---|---|---|
| 1 | B | 20 |
| 2 | C | 30 |
| 3 | G | 40 |

FIG.17

| TYPE OF LIQUID MEDICATION | CURRENT POSITION | MOVING TIME TO DISPENSING POSITION (s) |
|---|---|---|
| A | 8 | 3 |
| B | 1 | 0 |
| C | 2 | 3 |
| D | 3 | 6 |
| E | 4 | 9 |
| F | 5 | 12 |
| G | 6 | 9 |
| H | 7 | 6 |

FIG.18

| TYPE OF LIQUID MEDICATION | CURRENT POSITION | MOVING TIME TO DISPENSING POSITION (s) |
|---|---|---|
| A | 7 | 6 |
| B | 8 | 3 |
| C | 1 | 0 |
| D | 2 | 3 |
| E | 3 | 6 |
| F | 4 | 9 |
| G | 5 | 12 |
| H | 6 | 9 |

| TYPE OF LIQUID MEDICATION | CURRENT POSITION | MOVING TIME TO DISPENSING POSITION (s) |
|---|---|---|
| A | 3 | 6 |
| B | 4 | 9 |
| C | 5 | 12 |
| D | 6 | 9 |
| E | 7 | 6 |
| F | 8 | 3 |
| G | 1 | 0 |
| H | 2 | 3 |

LIQUID MEDICATION DISPENSING MACHINE

CROSS-REFERENCE TO RELATED APPLICATION

This application is a Divisional of U.S. application Ser. No. 13/993,499, filed on Jun. 12, 2013, and wherein U.S. application Ser. No. 13/993,499 is a national stage application filed under 35 U.S.C. § 371 of International Application No. PCT/JP2011/078524, filed on Dec. 9, 2011, which is based upon and claims the benefit of priority of the prior Japanese Patent Application No. 2010-292637, filed on Dec. 28, 2010, the entire contents of which are incorporated herein by reference.

TECHNICAL FIELD

The present invention relates to a liquid medication dispensing machine, and more particularly relates to a liquid medication dispensing machine for supplying a liquid medication from a liquid medication bottle containing the liquid medication to a prescription bottle.

BACKGROUND ART

Conventionally, a liquid medication as a liquid state medicine is dispensed in a dispensing pharmacy or the like. In accordance with a prescription for a patient, one or a plurality of types of liquid medications are infused sequentially by a predetermined quantity into a prescription bottle, and a required diluent is infused, thereby dispensing a liquid medication.

When preparing a liquid medication including suspensions, the prescription guidelines require that the liquid medication in a liquid medication bottle be stirred and then supplied to a prescription bottle. For stirring of a liquid medication, conventionally proposed is a structure having a rotary unit rotated while holding a plurality of liquid medication bottles, wherein a liquid medication bottle is inverted by rotating the rotary unit by 180 degrees (see e.g., Japanese Patent Laying-Open No. 2009-112673 (Patent Literature 1)). Another structure is proposed in which a nozzle is inserted into a liquid medication bottle containing a liquid medication, and the liquid medication is repeatedly sucked and discharged, thereby periodically stirring the liquid medication in the liquid medication bottle (see e.g., WO2010/110303 (Patent Literature 2)).

CITATION LIST

Patent Literature

PTL 1: Japanese Patent Laying-Open No. 2009-112673
PTL 2: WO2010/110303

SUMMARY OF INVENTION

Technical Problem

Patent Literature 1 discloses a flow of dispensing processing in which a prescription bottle is moved to a discharging position and a liquid medication bottle is then inverted to stir the liquid medication. However, in this dispensing processing, it is necessary to allow for a time for stirring the liquid medication before supply to the prescription bottle. Therefore, the time to supply the liquid medication to the prescription bottle becomes long disadvantageously.

The present invention was made in view of the above-described problem, and has a main object to provide a liquid medication dispensing machine by which the time to supply a liquid medication contained in a liquid medication bottle to a prescription bottle can be shortened.

Solution to Problem

A liquid medication dispensing machine according to an aspect of the present invention is a liquid medication dispensing machine supplying a liquid medication from a liquid medication bottle containing the liquid medication to a prescription bottle, including a liquid medication stirring unit that stirs the liquid medication in the liquid medication bottle, a bottle holding unit that holds a plurality of the liquid medication bottles including a first bottle containing a first liquid medication and a second bottle containing a second liquid medication, and a control unit that controls operation of the liquid medication dispensing machine. The control unit operates the liquid medication stirring unit to stir the second liquid medication while the first liquid medication is supplied from the first bottle to the prescription bottle.

In the liquid medication dispensing machine, preferably, the control unit starts supplying the second liquid medication from the second bottle to the prescription bottle after supply of the first liquid medication to the prescription bottle is completed.

In the liquid medication dispensing machine, preferably, the first liquid medication does not require stirring before supply to the prescription bottle.

The liquid medication dispensing machine preferably includes a bottle position changing unit that changes positions of the plurality of the liquid medication bottles held by the bottle holding unit. The control unit operates the liquid medication stirring unit to stir the second liquid medication while the bottle position changing unit changes the positions of the liquid medication bottles.

A liquid medication dispensing machine according to another aspect of the present invention includes a liquid medication supply unit that has a plurality of liquid medication bottles containing liquid medications and supplies the liquid medications from the liquid medication bottles to a prescription bottle, respectively. The liquid medications include a stirring-requiring liquid medication that requires stirring before supply to the prescription bottle. The liquid medication dispensing machine further includes a liquid medication stirring unit that stirs the liquid medications in the liquid medication bottles, and a control unit that causes the stirring-requiring liquid medication to be stirred by a time when a supply order of supplying the stirring-requiring liquid medication to the prescription bottle comes in a supply sequence in which the liquid medications contained in the plurality of liquid medication bottles are supplied from the liquid medication bottles to the prescription bottle, respectively.

In the liquid medication dispensing machine, preferably, the control unit causes the stirring-requiring liquid medication to be stirred while the liquid medication having the supply order earlier than the stirring-requiring liquid medication is supplied to the prescription bottle.

In the liquid medication dispensing machine, preferably, the liquid medications include a stirring-nonrequiring liquid medication that does not require stirring before supply to the prescription bottle. The control unit sets the supply sequence such that the supply order of the stirring-requiring liquid medication comes after the supply order of the stirring-nonrequiring liquid medication.

Advantageous Effects of Invention

According to the liquid medication dispensing machine of the present invention, the time to supply a liquid medication to a prescription bottle can be shortened.

BRIEF DESCRIPTION OF DRAWINGS

FIG. 11 shows an example of a table indicating the current position of each liquid medication bottle.

FIG. 12 shows an example of a table indicating liquid medications that require stirring.

FIG. 17 is a table showing the current position of each liquid medication bottle when liquid medication B is located at a dispensing position.

FIG. 18 is a table showing the current position of each liquid medication bottle when liquid medication C is located at the dispensing position.

DESCRIPTION OF EMBODIMENTS

Figure 1:
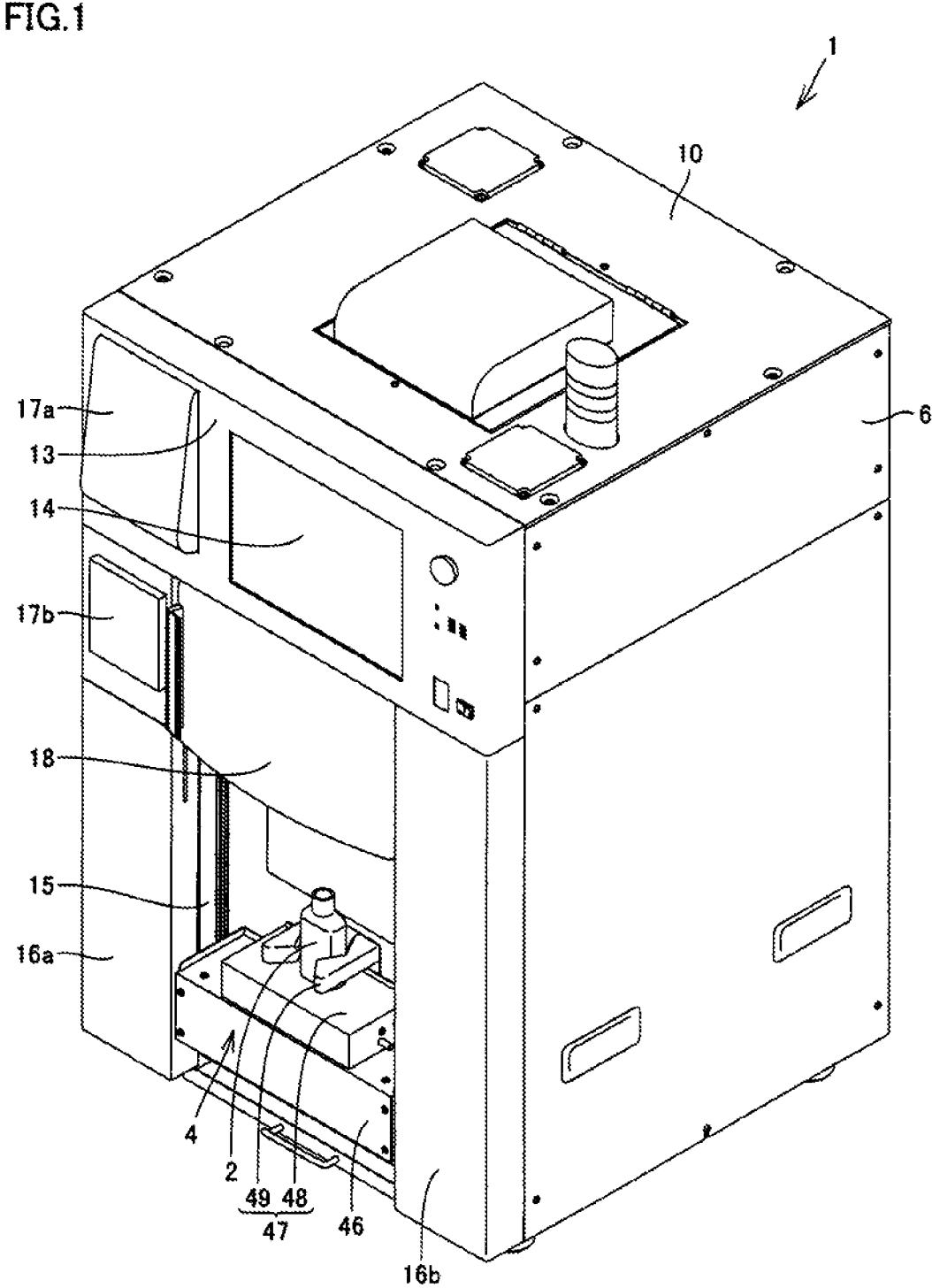
FIG. 1 is a perspective view showing a structure of a liquid medication dispensing machine 1 of one embodiment of the present invention.

Embodiments of the present invention will be described below based on the drawings. In the following drawings, the same or corresponding portions have the same reference characters allotted, and description thereof will not be repeated.

First Embodiment

Figure 2:
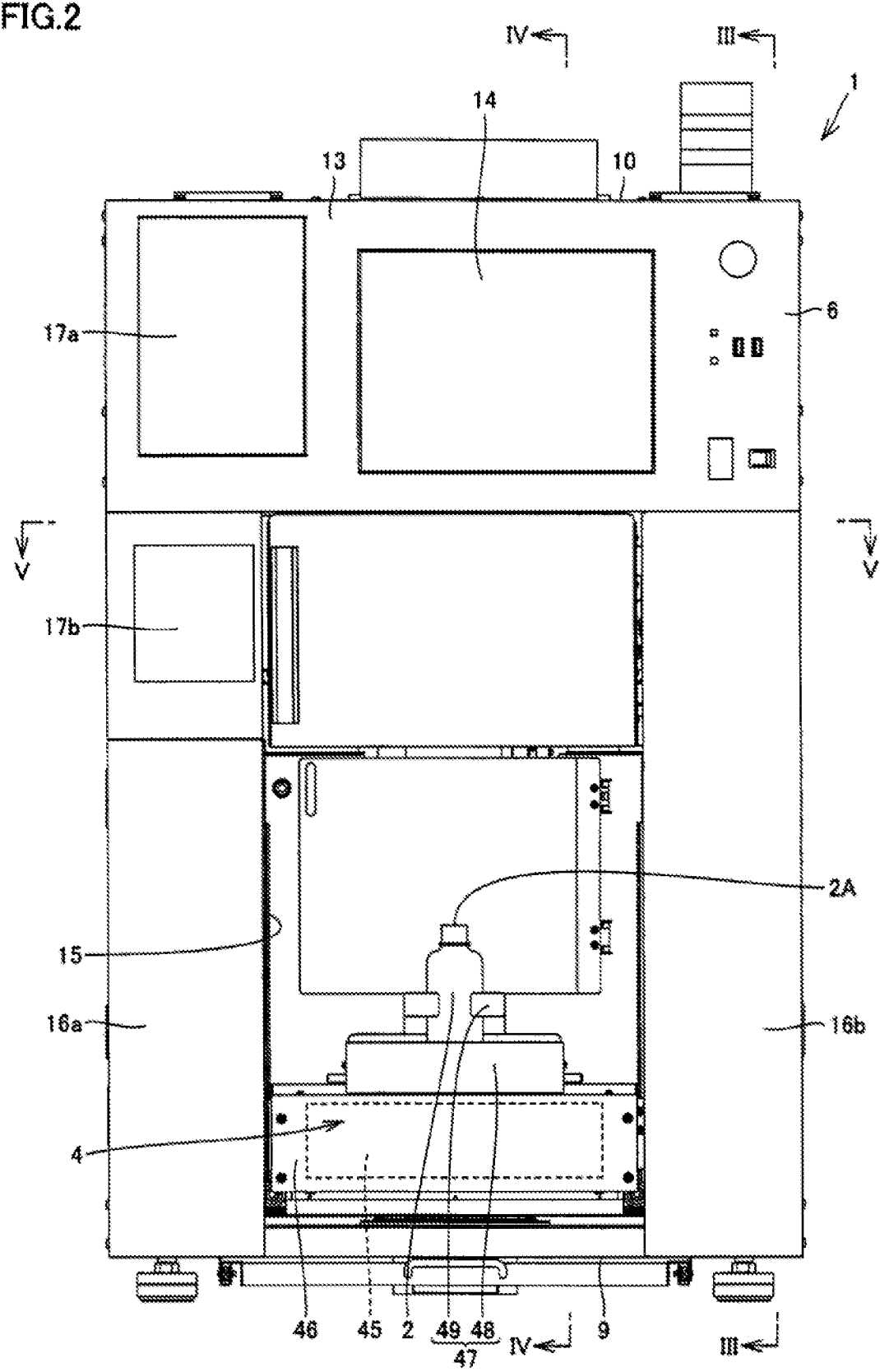
FIG. 2 is a front view of the liquid medication dispensing machine shown in FIG. 1.
Figure 3:
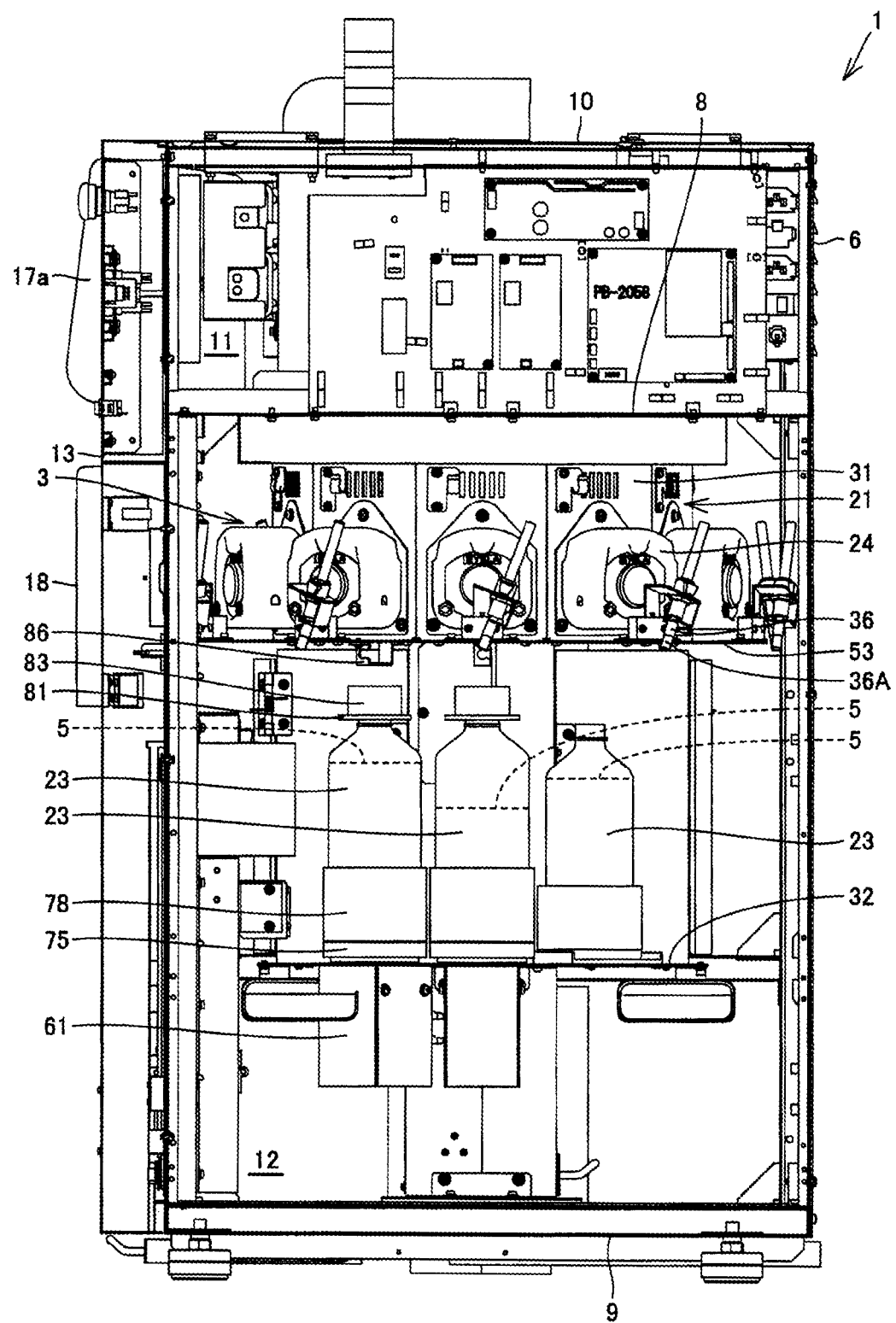
FIG. 3 is a cross sectional view of the liquid medication dispensing machine taken along the line shown in FIG. 2.
Figure 4:
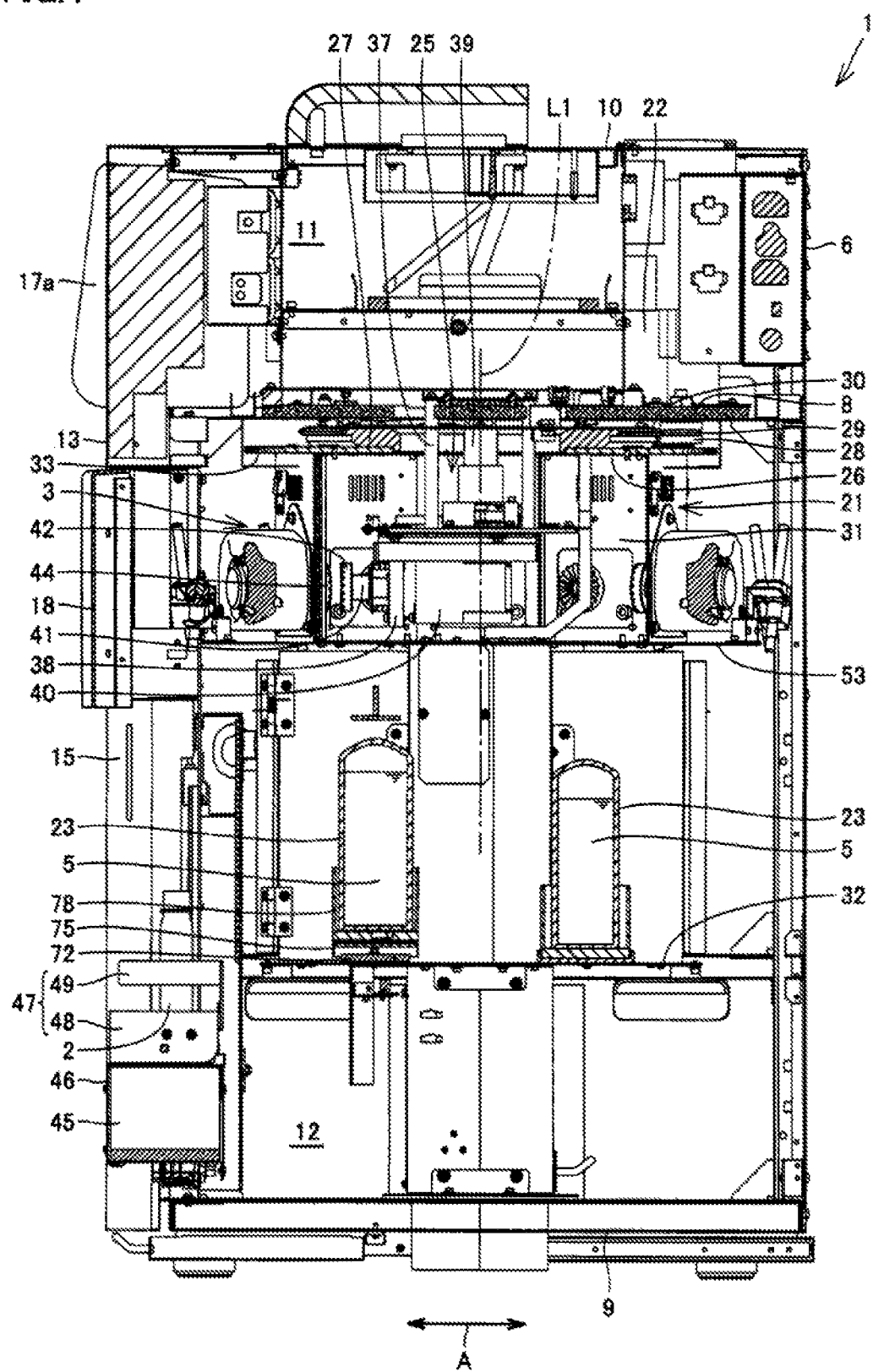
FIG. 4 is a cross sectional view of the liquid medication dispensing machine taken along the line IV-IV shown in FIG. 2.
Figure 5:
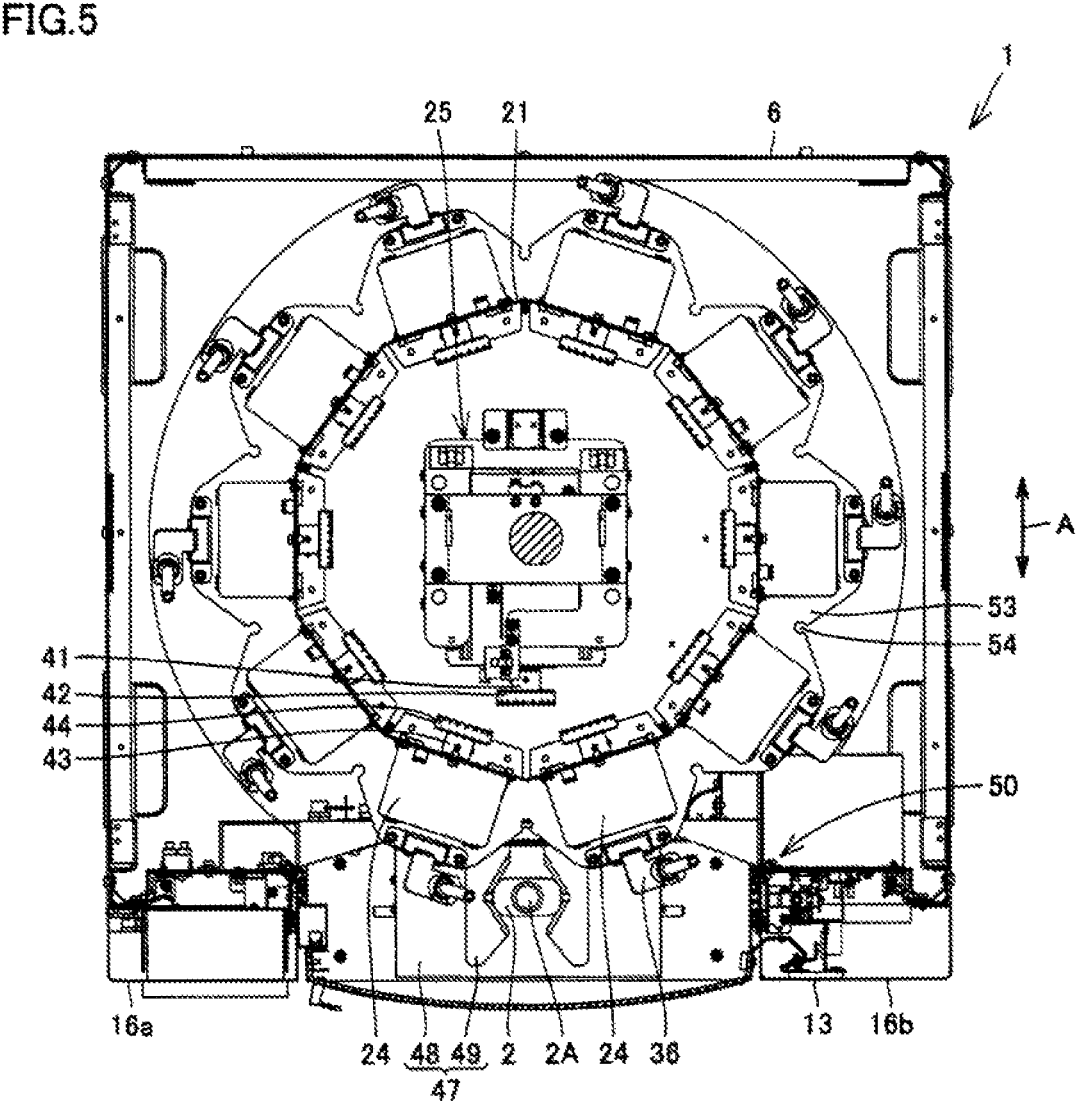
FIG. 5 is a cross sectional view of the liquid medication dispensing machine taken along the line V-V shown in FIG. 2.

FIG. 1 is a perspective view showing a structure of a liquid medication dispensing machine 1 of one embodiment of the present invention. FIG. 2 is a front view of liquid medication dispensing machine 1 shown in FIG. 1. FIG. 3 is a cross sectional view of liquid medication dispensing machine 1 taken along the line shown in FIG. 2. FIG. 4 is a cross sectional view of liquid medication dispensing machine 1 taken along the line IV-IV shown in FIG. 2. FIG. 5 is a cross sectional view of liquid medication dispensing machine 1 taken along the line V-V shown in FIG. 2. Liquid medication dispensing machine 1 of the present embodiment is used to supply and dispense a liquid medication 5 which is a liquid state medicine from a liquid medication bottle 23 containing liquid medication 5 to a prescription bottle 2 in accordance with a prescription for a patient.

Liquid medication dispensing machine 1 includes a liquid medication supply unit 3 having a plurality of liquid medication bottles 23 each containing liquid medication 5 and supplying liquid medication 5 from each of liquid medication bottles 23 to prescription bottle 2 and a weight detection unit 4 detecting the weight of liquid medication 5 contained in prescription bottle 2. The volume of liquid medication 5 supplied to prescription bottle 2 is calculated from the weight of liquid medication 5 detected by weight detection unit 4 and the specific gravity of liquid medication 5. Liquid medication supply unit 3 is controlled such that a predetermined volume of liquid medication 5 in accordance with the prescription is supplied to prescription bottle 2. Liquid medication supply unit 3 and weight detection unit 4 are provided in a housing 6. Housing 6 has a rectangular parallelepiped shape, and is installed on a horizontal installation surface in an upright position.

A support frame 8 is provided inside housing 6. Support frame 8 is located between a bottom plate 9 of housing 6 and a top plate 10 of housing 6, and in more detail, located closer to top plate 10 of housing 6. The internal space of housing 6 is divided by support frame 8 into an upper space 11 above support frame 8 and a lower space 12 below support frame 8. A touch panel 14 and printers 17a, 17b are located in a front section 13 of housing 6. A lower opening 15 by which lower space 12 communicates with the outside of housing 6 is also formed in front section 13.

Lower opening 15 is formed between both side portions 16a, 16b in front section 13 of housing 6. Above lower opening 15 between both side portions 16a, 16b, a curved plate-like front cover portion 18 is located which separates lower space 12 and the outside of housing 6. Front cover portion 18 is made of a transparent material such that lower space 12 is visible from outside the front side of housing 6. Front cover portion 18 is attached to one of both side portions 16a, 16b with a hinge and is provided to be pivotable around the axis of the hinge, so that front cover portion 18 can be opened/closed.

Liquid medication supply unit 3 has a rotation drum 21 which is a rotator located in lower space 12 and provided rotatably around an axis line (hereinbelow a "drum axis line") L1 perpendicular to support frame 8 and a drum rotating motor 22 mounted on the upper surface of support frame 8 and rotating rotation drum 21 around drum axis line L1 relative to support frame 8. Liquid medication supply unit 3 also has a plurality of pumps 24 provided for rotation drum 21 and transporting a liquid medication from a plurality of liquid medication bottles 23 containing liquid medication 5 to prescription bottle 2, and a pump driving unit 25 driving each pump 24. Each pump 24 may be a tube pump.

Rotation drum 21 has a pump holder 31 holding each pump 24 and a liquid medication bottle holder 32 as a bottle holding unit holding plurality of liquid medication bottles 23 in an upright position such that an opening 23A (see FIG. 8 which will be described later) is open upward. Liquid medication bottle holder 32 is provided below pump holder 31 and has an annular flat plate shape in plan view. On pump holder 31, respective pumps 24 are located at intervals in a circumferential direction around drum axis line L1 (hereinbelow a "drum circumferential direction"). On liquid medication bottle holder 32, respective liquid medication bottles 23 are located at intervals in the drum circumferential direction.

The number of liquid medication bottles 23 and pumps 24 mounted on rotation drum 21 in the present embodiment can be optionally changed according to the purpose. A different liquid medication 5 may be contained in each of plurality of liquid medication bottles 23, or heavily used liquid medication 5 of the same type may be contained in plurality of liquid medication bottles 23, or a diluent, such as water or simple syrup, may be contained in one or a plurality of liquid medication bottles 23.

Pump driving unit 25 for selectively driving each pump 24 has a fixed part 37 fixed to support frame 8, a moving part 38 provided movably forward and backward relative to fixed part 37 (in the direction of a double-headed arrow A shown in FIGS. 4 and 5), a moving motor 39 which is fixed to fixed part 37 and moves moving part 38 forward and backward relative to fixed part 37, and a pump driving motor 40 which is fixed to moving part 38 and drives pump 24. Pump driving motor 40 may be implemented by a stepping motor.

A coupling member 42 is fixed at the leading end of drive shaft 41 rotated by pump driving motor 40. A coupled member 44 to be coupled to coupling member 42 is fixed to a rotary shaft 43 of the rotor of each pump 24. When coupling member 42 and coupled member 44 are coupled to each other, rotation of pump driving motor 40 is transmitted to pump 24. Each pump 24 is constructed to be driven individually in conjunction with intermittent driving of drum rotating motor 22. The speed of supply of liquid medication 5 to prescription bottle 2 increases as the speed of rotation of pump driving motor 40 increases.

By driving moving motor 39, pump driving motor 40 is moved forward and backward. By this movement of pump driving motor 40, a switch can be made between a coupled state in which coupling member 42 of pump driving motor 40 is coupled to coupled member 44 of pump 24 and a decoupled state in which coupling member 42 is not coupled to coupled member 44.

For example, coupling member 42 and coupled member 44 can be coupled to each other by advancing moving part 38 by driving of moving motor 39. The coupling of coupling member 42 and coupled member 44 can be released by retracting moving part 38 by driving of moving motor 39. Rotation drum 21 can be rotated relative to support frame 8 in the decoupled state.

By driving drum rotating motor 22 in the decoupled state, rotation drum 21 is rotated to a position where coupled member 44 of a specific pump 24 selected based on prescription information input to liquid medication dispensing machine 1 faces coupling member 42 of pump driving motor 40, and after the rotation, a switch is made to the coupled state. The selected specific pump 24 can thereby be driven to dispense liquid medication 5 supplied from a desired liquid medication bottle 23 into prescription bottle 2. Although coupling member 42 and coupled member 44 are both implemented by gears, they may have any structure that can transmit motive power.

At an upper end 26 of rotation drum 21, a ring member 27 located horizontally and coaxially with drum axis line L1 is located rotatably around drum axis line L1. Three or more support members 28 supporting ring member 27 are provided on the outer circumferential side of ring member 27. Respective support members 28 are located at equal intervals in the drum circumferential direction.

Respective support members 28 are provided relatively rotatably with respect to support frame 8 around an axis line parallel to drum axis line L1. A recessed groove 29 is formed in the flat cylindrical outer circumferential surface of each of support members 28 along the entire circumference. An annular protruding line 30 is formed in the outer circumferential part of ring member 27 along the entire circumference. Protruding line 30 of ring member 27 is fitted into recessed groove 29 of each support member 28. Ring member 27 and support member 28 are provided relatively rotatably.

Drum rotating motor 22 is fixed to support frame 8. A driving gear (not shown) is fixed to the rotary shaft of drum rotating motor 22. A driven gear 33 meshing with the driving gear is fixed to upper end 26 of rotation drum 21. Driven gear 33 has an annular thin plate shape and is fixed to the lower surface of ring member 27. Rotation of drum rotating motor 22 is transmitted to ring member 27 via the driving gear and driven gear 33, and ring member 27 and rotation drum 21 to which the ring member is fixed are thereby rotated integrally. With such a structure, rotation drum 21 can be smoothly rotated relative to support frame 8.

Drum rotating motor 22 revolves integrally in the horizontal direction plurality of liquid medication bottles 23 mounted on rotation drum 21, pumps 24 and supply nozzles 36 provided in correspondence with plurality of liquid medication bottles 23, respectively, and a tube 34, which will be described later, with one end located inside liquid medication bottle 23 and the other end attached to supply nozzle 36. Rotation drum 21 serves as a bottle position changing unit that changes the positions of a plurality of liquid medication bottles 23 held by liquid medication bottle holder 32 in housing 6 of liquid medication dispensing machine 1.

Supply nozzle 36 is attached onto the same circumference as the outer circumferential part of a nozzle attachment plate 53 which is an annular flat plate provided at the lower end of pump holder 31. Respective supply nozzles 36 are located on nozzle attachment plate 53 at equal intervals in the drum circumferential direction on a virtual circle around drum axis line L1. Supply nozzle 36 is attached to nozzle attachment plate 53 at an inclination of a predetermined angle with respect to drum axis line L1. Nozzle attachment plate 53 is located above liquid medication bottle holder 32. Nozzle attachment plate 53 and liquid medication bottle holder 32 are parallel to each other, and are constructed to be capable of revolving on a horizontal plane together with rotation drum 21 around drum axis line L1.

Weight detection unit 4 is located in lower opening 15. Weight detection unit 4 has an electronic balance 45, a casing 46 storing electronic balance 45, and a prescription bottle holder 47 mounted on and fixed to electronic balance 45 and holding prescription bottle 2 in an upright position such that an opening 2A is open upward. Electronic balance 45 detects the weight of liquid medication 5 supplied to prescription bottle 2. When the weight of liquid medication 5 reaches a predetermined value, liquid medication supply unit 3 stops driving of pump 24 to stop supply of liquid medication 5 to prescription bottle 2. Electronic balance 45 may be of any type, such as tuning fork, load cell or electromagnetic type. Casing 46 is provided at a lower position of front section 13 of housing 6 between both side portions 16a, 16b. Prescription bottle holder 47 has a table 48 on which prescription bottle 2 is mounted and a holding fixture 49 provided above table 48 and holding prescription bottle 2.

Weight detection unit 4 is moved up and down by an elevating device 50 as a driving unit shown in FIG. 5. Elevating device 50 moves weight detection unit 4 in the vertical direction so as to be located at two positions, an initial position and a supply position, and accordingly moves prescription bottle 2 mounted on table 48 of weight detection unit 4. The initial position is a position where prescription bottle 2 is placed on table 48 of liquid medication dispensing machine 1. The supply position is a position where prescription bottle 2 and supply nozzle 36 come closer to each other than at the initial position so that liquid medication 5 is supplied to prescription bottle 2. By means of elevating device 50, prescription bottle 2 is reciprocally moved between the outside and the inside of housing 6 of liquid medication dispensing machine 1 so as to reciprocate between the initial position and the supply position.

Figure 6:
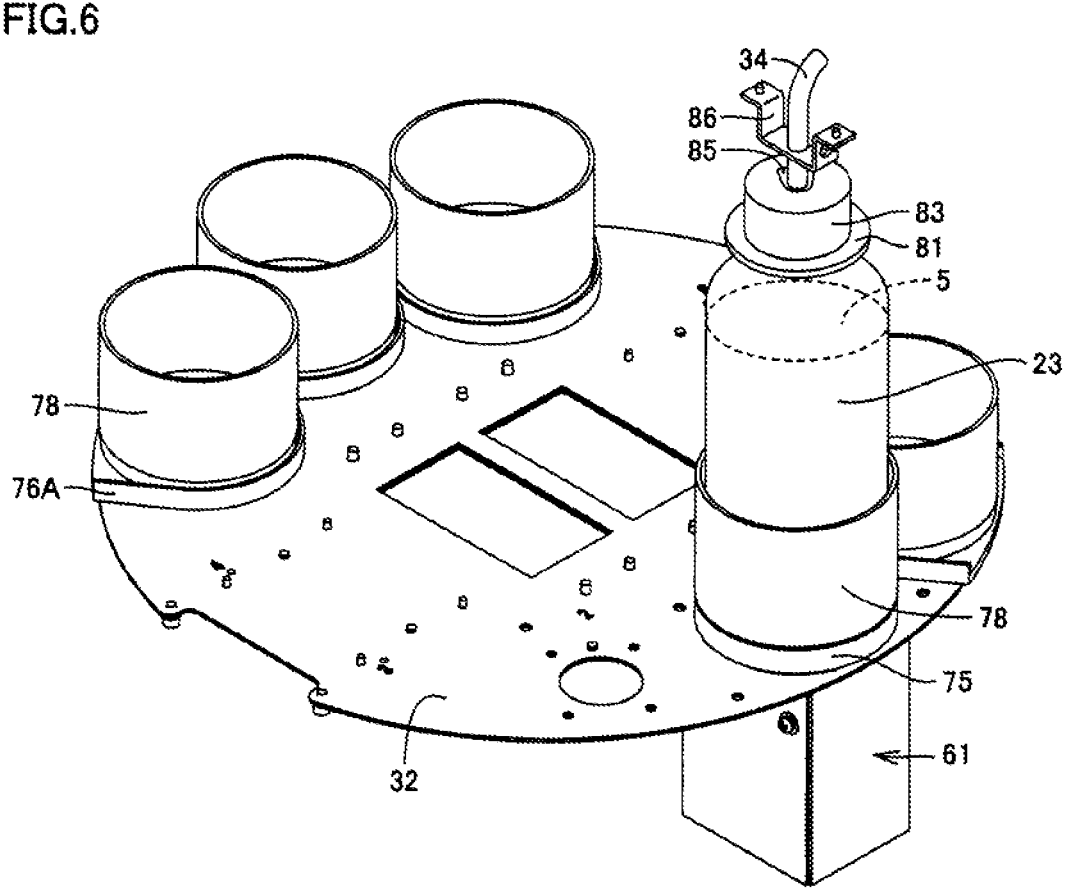
FIG. 6 is a perspective view showing a structure of a stirring unit by which a liquid medication in a liquid medication bottle is stirred.
Figure 7:
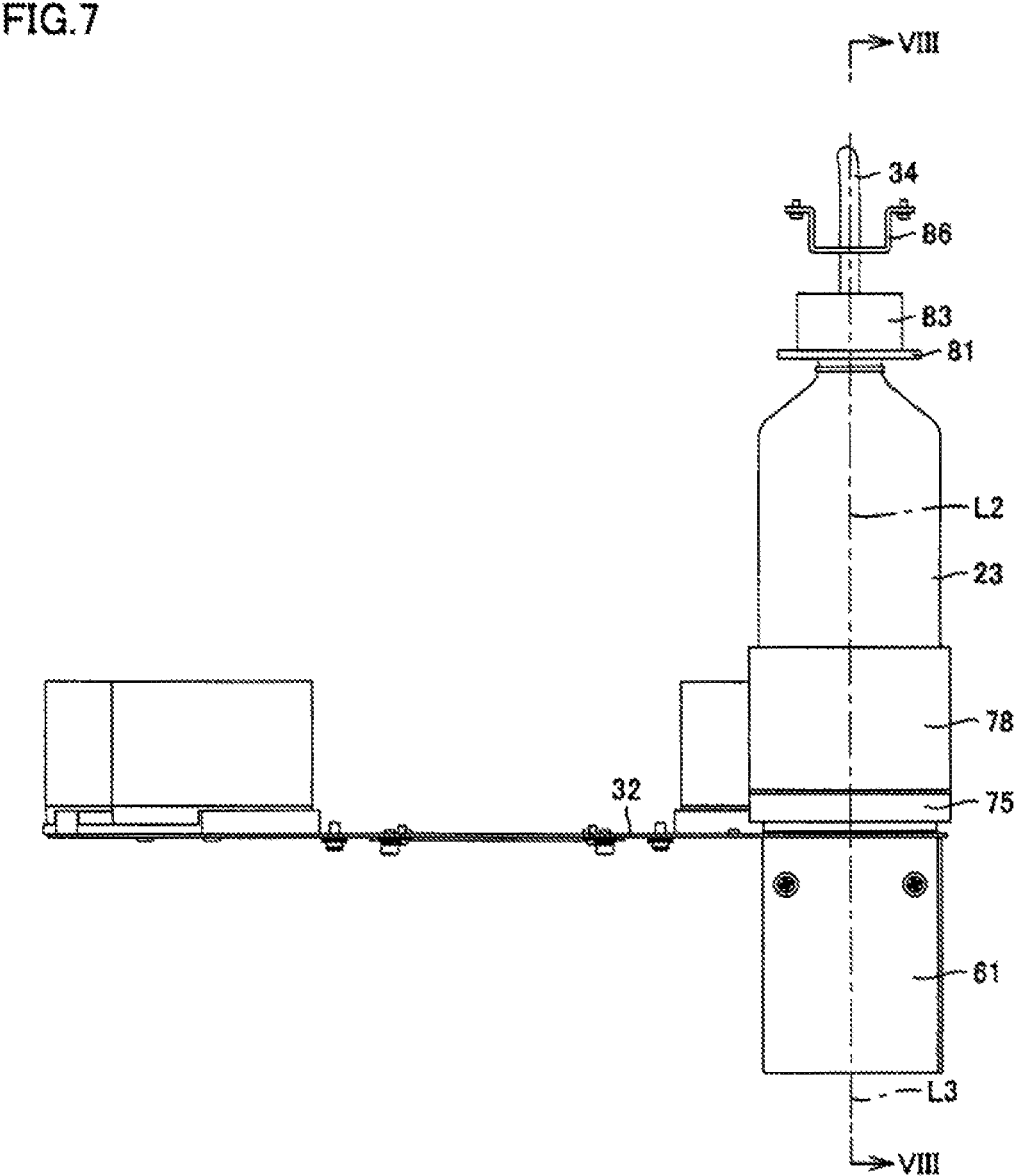
FIG. 7 is a side view of the stirring unit shown in FIG. 6.
Figure 8:
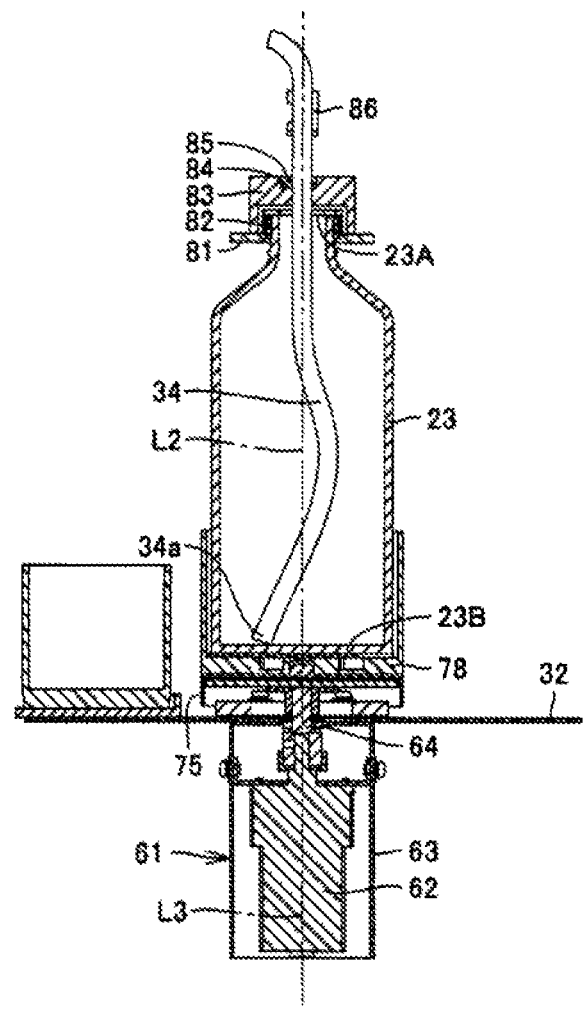
FIG. 8 is a cross sectional view of the stirring unit taken along the line VIII-VIII shown in FIG. 7.

FIG. 6 is a perspective view showing a structure of a stirring unit by which liquid medication 5 in liquid medication bottle 23 is stirred. FIG. 7 is a side view of the stirring unit shown in FIG. 6. FIG. 8 is a cross sectional view of the stirring unit taken along the line VIII-VIII shown in FIG. 7. Liquid medication supply unit 3 of the present embodiment includes, in housing 6 of liquid medication dispensing machine 1, a liquid medication stirring unit stirring liquid medication 5 contained in liquid medication bottle 23. This liquid medication stirring unit will be described in detail below.

In FIGS. 6 to 8, liquid medication bottle holder 32 with merely one liquid medication bottle 23 mounted thereon is shown giving priority to clarity. Although liquid medication dispensing machine 1 includes a plurality of cup fixing parts 76, 76A, cups 78 and the like for holding liquid medication bottles 23, merely some of plurality of cup fixing parts 76, 76A, cups 78 and the like are illustrated in FIGS. 6 and 7, and not all of them are illustrated.

A rotationally driving unit 61 generating rotary force is located under liquid medication bottle holder 32. As shown in FIG. 8, rotationally driving unit 61 has a motor 62 as an example of a power source and a box 63 storing motor 62 therein. A shaft 64 rotating with motor 62 is coupled to the rotary shaft of motor 62. Shaft 64 is fixed to motor 62 rotatably around a rotation axis L3 integrally with motor 62. Shaft 64 is located to extend from the inside to the outside of box 63. Shaft 64 is located to extend through flat plate-like liquid medication bottle holder 32 in the vertical direction, and transmits rotary force generated by motor 62 from the lower side of liquid medication bottle holder 32 to the upper side of liquid medication bottle holder 32.

Cover 75 surrounds the circumference of shaft 64 and covers the upper end of shaft 64. Cup 78 is integrally fixed to shaft 64 with cover 75 interposed therebetween. Cup 78 has a bottomed hollow cylindrical shape. Cup 78 serves as a holder holding liquid medication bottle 23. Cup 78 holds the bottom 23B side of liquid medication bottle 23 shown in FIG. 8. Liquid medication bottle 23 is received in cup 78 such that bottom 23B is opposed to the inner bottom surface of cup 78. The inner wall surface of the sidewall of cup 78 has a diameter slightly larger than that of the side surface of liquid medication bottle 23. Therefore, the side surface of liquid medication bottle 23 is opposed to the inner wall surface of the sidewall of cup 78 with a minute clearance. Part of the side surface of liquid medication bottle 23 may contact the inner wall surface of the sidewall of cup 78.

Tube 34 as a pipe part is located inside liquid medication bottle 23. Tube 34 is provided for each of plurality of liquid medication bottles 23. Tube 34 is made of a material having flexibility and elasticity, and is deformable in cross section under pressure and is elastically restored by releasing pressure. Tube 34 may be made of synthetic resin, such as a silicon tube, for example. Tube 34 extends from opening 23A toward bottom 23B of liquid medication bottle 23, and is located inside liquid medication bottle 23 such that its one end 34a contacts the inner surface of bottom 23B of liquid medication bottle 23.

A base member 81 is fixed to opening 23A of liquid medication bottle 23. Tube 34 is inserted into a through-hole formed in base member 81, and is located to extend from the outside to the inside of liquid medication bottle 23. Base member 81 is fixed to opening 23A of liquid medication bottle 23 as shown in FIG. 8. A cylindrical spacer 82 made of an elastic material, such as silicone rubber, for example, is attached to the inner circumferential surface of base member 81. Base member 81 is attached to liquid medication bottle 23 with elastically deformable spacer 82 interposed therebetween such that base member 81 can be reliably fixed to opening 23A of liquid medication bottle 23 even if dimensional variations in base member 81 or liquid medication bottle 23 occur.

A cover 83 is located over base member 81. Cover 83 is mounted on the upper surface of base member 81 while not being fixed to base member 81. Cover 83 has a cap shape having a hollow cylindrical wall portion and a disk-like top portion covering the upper end of the wall portion. The lower end of the wall portion comes into contact with the upper surface of base member 81, so that cover 83 is mounted over base member 81. Cover 83 is provided to cover opening 23A of liquid medication bottle 23 while cover 83 is mounted on base member 81 fixed to liquid medication bottle 23. A through-hole having a diameter of such a degree that tube 34 can be just inserted therethrough is formed in the above-mentioned top portion of cover 83.

The above-mentioned top portion of cover 83 further has a recess 84 obtained by recessing part of the upper surface. A positioning member 85 is attached to tube 34. Positioning member 85 is attached to tube 34 so as not to block the flow of liquid medication 5 flowing through the inside of tube 34. Moreover, positioning member 85 is attached to tube 34 so as to be unlikely to move relative to tube 34 in the longitudinal direction of tube 34. Recess 84 and positioning member 85 have a corresponding shape such that positioning member 85 is fitted within recess 84.

Positioning member 85 is engaged with recess 84 formed in cover 83 to thereby position tube 34 with positioning member 85 attached thereto relative to liquid medication bottle 23. As shown in FIG. 8, when positioning member 85 is received in recess 84 of cover 83, positioning member 85 positions tube 34 relative to liquid medication bottle 23 such that one end 34a of tube 34 slightly curved inside liquid medication bottle 23 contacts bottom 23B of liquid medication bottle 23.

Furthermore, a tube fixing part 86 for fixing tube 34 on the outside of liquid medication bottle 23 is provided. Tube fixing part 86 is fixed to the lower surface side of nozzle attachment plate 53 as shown in FIG. 3. By causing tube fixing part 86 to hold tube 34 with tube 34 inserted into liquid medication bottle 23 as illustrated in FIGS. 7 and 8, tube 34 is fixed to nozzle attachment plate 53. Furthermore, tube 34 is fitted within a cutout 54 (see FIG. 5) formed in nozzle attachment plate 53, and is thereby fixed to nozzle attachment plate 53.

In the liquid medication stirring unit having the structure described above, when motor 62 of rotationally driving unit 61 is driven, shaft 64 fixed to motor 62 is rotated together with motor 62. The direction of rotation of motor 62 at this time will be called a forward direction. Cup 78 fixed to shaft 64 and liquid medication bottle 23 held by cup 78 are rotated around rotation axis L3 along with the rotation of shaft 64 in the forward direction. Rotation axis L3 forming the central axis of rotation of liquid medication bottle 23 extends along a center line L2 of liquid medication bottle 23. Here, center line L2 of liquid medication bottle 23 refers to a straight line connecting opening 23A and bottom 23B of liquid medication bottle 23, and typically refers to a straight line connecting the center of opening 23A of liquid medication bottle 23 of circular shape in plan view and the center of bottom 23B of liquid medication bottle 23 of circular shape in plan view.

In the embodiment illustrated in FIGS. 7 and 8, liquid medication bottle 23 is located at the center of cup 78. Center line L2 of liquid medication bottle 23 and rotation axis L3 of rotationally driving unit 61 thus reside on the same straight line. It is noted that, in order to stir liquid medication 5 more efficiently, center line L2 of liquid medication bottle 23 may be offset from rotation axis L3 of rotationally driving unit 61, or center line L2 of liquid medication bottle 23 may be inclined with respect to rotation axis L3 of rotationally driving unit 61.

Along with the rotation of this liquid medication bottle 23, liquid medication 5 contained in liquid medication bottle 23 flows inside liquid medication bottle 23 in the circumferential direction of the cylindrical side portion of liquid medication bottle 23 in the direction of rotation of liquid medication bottle 23.

After motor 62 is rotated for a predetermined time in the forward direction, motor 62 is subsequently rotated in the reverse direction opposite to the forward direction. Rotationally driving unit 61 is provided so as to be capable of generating rotary force both in the forward and reverse directions. Liquid medication dispensing machine 1 may be constructed to allow an operator who operates liquid medication dispensing machine 1 to optionally set the direction of rotation and time of rotation of motor 62. For example, the time of rotation of motor 62 in the forward direction and the time of rotation in the reverse direction may be made equal, such as by rotating motor 62 in the forward direction for 5 seconds to rotate liquid medication bottle 23 several times, and then rotating motor 62 in the reverse direction for 5 seconds to rotate liquid medication bottle 23 several times in the reverse direction. Alternatively, for example, the direction of rotation of motor 62 may be set to be the forward direction alone.

Along with the change of the direction of rotation of motor 62, the direction of rotation of liquid medication bottle 23 is also changed. That is, rotationally driving unit 61 rotates liquid medication bottle 23 in the forward direction, and then rotates liquid medication bottle 23 in the reverse direction opposite to the forward direction. Inside liquid medication bottle 23 having been changed in the direction of rotation and being rotated in the reverse direction, the turbulence intensity of a turbulent flow in the flow of liquid medication 5 increases. In addition, a vortex occurs in the flow of liquid medication 5. Liquid medication 5 is stirred inside liquid medication bottle 23 by the action of this turbulent flow and vortex.

In this way, liquid medication 5 contained in liquid medication bottle 23 can be stirred inside liquid medication dispensing machine 1 by rotating liquid medication bottle 23 by the rotation driving power generated by rotationally driving unit 61. Therefore, liquid medication 5 which needs stirring can be dispensed efficiently in a short time through the use of liquid medication dispensing machine 1 of the present embodiment. With a simple structure obtained by adding rotationally driving unit 61 to a conventional device, cup 78 holding liquid medication bottle 23 and liquid medication bottle 23 can be rotated integrally to stir liquid medication 5 inside liquid medication dispensing machine 1. Since the turbulence intensity of the turbulent flow in liquid medication bottle 23 can be increased by switching the direction of rotation of liquid medication bottle 23 from the forward direction to the reverse direction, liquid medication 5 can be stirred more efficiently.

Tube 34 is located inside liquid medication bottle 23 to extend from opening 23A to bottom 23B of liquid medication bottle 23, and tube 34 is fixed on the outside of liquid medication bottle 23. Therefore, tube 34 is relatively rotated with respect to liquid medication bottle 23 being rotated. Since tube 34 is kept fixed relative to liquid medication 5 flowing through the inside of liquid medication bottle 23 together with liquid medication bottle 23, tube 34 serves as a stirrer for liquid medication 5. That is, by locating tube 34 inside liquid medication bottle 23 to be immersed in liquid medication 5, the flow of liquid medication 5 is more likely to become a turbulent flow. Liquid medication 5 can therefore be stirred more efficiently.

Figure 9:
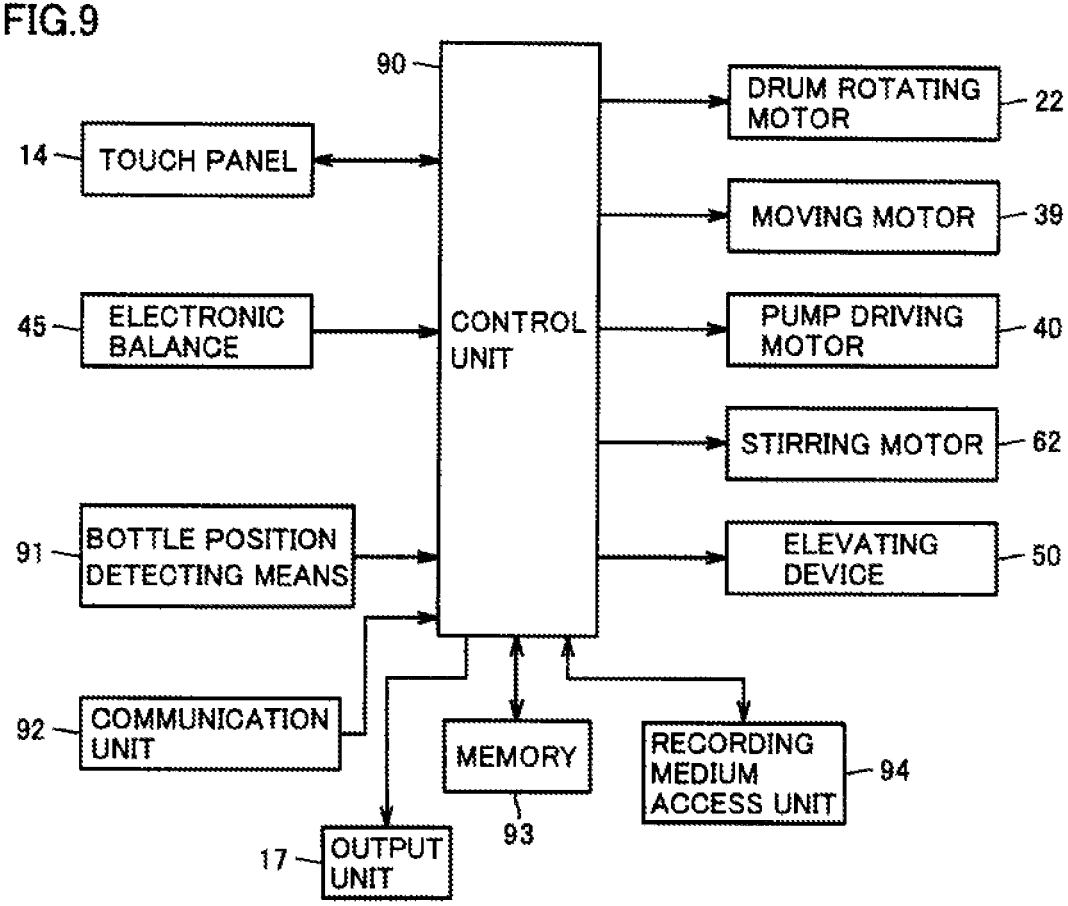
FIG. 9 is a block diagram showing a structure of the liquid medication dispensing machine.

Next, control exerted in the case of supplying liquid medication 5 from liquid medication bottle 23 to prescription bottle 2 for dispensing will be described. FIG. 9 is a block diagram showing a structure of liquid medication dispensing machine 1. As shown in FIG. 9, liquid medication dispensing machine 1 includes a control unit 90 that controls the operation of liquid medication dispensing machine 1 as a whole. Touch panel 14 serves as an input unit on which various parameters related to the operation of liquid medication dispensing machine 1, such as prescription data, and various types of information, such as patient's name and pharmacist's name, are input. Touch panel 14 also serves as a display unit that displays the operating state of liquid medication dispensing machine 1. Liquid medication dispensing machine 1 may include, as a display unit, a lamp that lights up when a malfunction of liquid medication dispensing machine 1 occurs, for example, in addition to touch panel 14.

Electronic balance 45 detects the weight of liquid medication 5 supplied to prescription bottle 2 and inputs the value of the detected weight to control unit 90. Control unit 90 supplies a predetermined quantity of liquid medication 5 to prescription bottle 2 while receiving weight data of liquid medication 5 in prescription bottle 2 from electronic balance 45.

Liquid medication dispensing machine 1 includes bottle position detecting means 91 that detects the position of each liquid medication bottle 23 in lower space 12 inside housing 6. Bottle position detecting means 91 may be any type of sensor, for example, and the sensor may detect the rotation angle around drum axis line L1 of liquid medication bottle holder 32. Liquid medication bottle 23 is rotationally moved around drum axis line L1 with the rotation of rotation drum 21. Thus, the current position of liquid medication bottle 23 changes frequently. Bottle position detecting means 91 is used to accurately detect the current position of liquid medication bottle 23, and data on the detected current position of liquid medication bottle 23 is input to control unit 90.

Liquid medication dispensing machine 1 also includes a communication unit 92 for making communications with external equipment to receive data from the external equipment. Various parameters related to the operation of liquid medication dispensing machine 1 may be input to control unit 90 by the operation on touch panel 14 described above, or alternatively may be input to control unit 90 from an external computer via communication unit 92.

Liquid medication dispensing machine 1 also includes a memory 93 for control unit 90 to perform calculations. Memory 93 may store data on the current position of liquid medication bottle 23 and data on liquid medication 5 contained in liquid medication bottle 23 loaded in liquid medication dispensing machine 1. Liquid medication dispensing machine 1 also includes a recording medium access unit 94 for loading a removable recording medium. The above-described data on liquid medication 5 may be stored in any recording medium loaded in recording medium access unit 94 and may be read appropriately from the recording medium by control unit 90.

Control unit 90 controls liquid medication dispensing machine 1 based on information input from the various types of devices described above. Specifically, control signals are transmitted from control unit 90 to drum rotating motor 22, moving motor 39, pump driving motor 40, motor 62 for stirring liquid medication 5, and elevating device 50. Each motor operates and stops appropriately, so that liquid medication 5 is supplied from liquid medication bottle 23 to prescription bottle 2. Upon termination of supply of liquid medication 5, a piece of paper with a dispensing result printed thereon and a label to be affixed to prescription bottle 2 with patient's name, pharmacy's name, time of taking medicine, dose, and the like printed thereon are output from printers 17a, 17b constituting an output unit 17.

Figure 10:
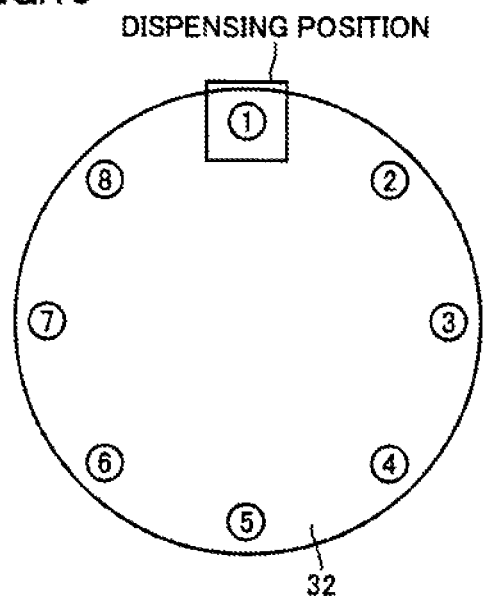
FIG. 10 is a schematic view showing the position of each liquid medication bottle.

FIG. 10 is a schematic view showing the position of each liquid medication bottle 23 detected by bottle position detecting means 91. FIG. 11 shows an example of a table indicating the current position of each liquid medication bottle 23. As shown in FIG. 10, eight liquid medication bottles 23 shall be mountable on liquid medication bottle holder 32 of the present embodiment. The positions at which these eight liquid medication bottles 23 are mounted on liquid medication bottle holder 32 are denoted by the numbers 1 to 8 in FIG. 10, respectively. The position denoted by the number 1 is a position on the forefront side of liquid medication dispensing machine 1 at which liquid medication 5 contained in liquid medication bottle 23 is discharged to a prescription bottle. This position will be called a dispensing position.

As shown in FIG. 11, eight liquid medication bottles 23 currently loaded in liquid medication dispensing machine 1 contain eight types of liquid medications A to H, respectively. At this time, liquid medication bottle 23 containing liquid medication A shall be located at the dispensing position. Rotation drum 21 shall be rotatable to the both sides in the drum circumferential direction. Liquid medication bottle holder 32 is rotatable both in the clockwise direction and the counterclockwise direction. Therefore, liquid medication B and liquid medication H arranged next to liquid medication A currently located at the dispensing position are moved to the dispensing position in an equal time.

In the following examples, suppose the time required to rotate liquid medication bottle holder 32 by 45°, namely, the time required to move liquid medication B next to liquid medication A currently located at the dispensing position to the dispensing position, to be 3 seconds. In this case, the moving time increases in proportion to the moving distance of liquid medication bottle 23. As shown in FIG. 11, the moving time for liquid medication C and liquid medication G, which are the second medications away from liquid medication A, to the dispensing position is 6 seconds. Similarly, the moving time for liquid medication E, which is most distant from liquid medication A in the direction of rotation, to the dispensing position is 12 seconds.

FIG. 12 shows an example of a table indicating liquid medications 5 that require stirring. Among eight type of liquid medications A to H loaded in liquid medication dispensing machine 1, liquid medication B and liquid medication E are stirring-requiring liquid medications that require stirring before supply to prescription bottle 2. In the present embodiment, a liquid medication that requires stirring refers to a liquid medication that will be heterogeneous by precipitation or the like if left at rest for a long time. The liquid medication that requires stirring includes a suspension or an emulsion, for example. In contrast, liquid medications A, C, D, and F to H are stirring-nonrequiring liquid medications that do not require stirring before supply to prescription bottle 2. The liquid medication that does not require stirring is a liquid medication that can maintain a homogeneous state even if left at rest for a long time.

As shown in FIG. 12, the stirring time required for liquid medication B and liquid medication E is set at 10 seconds. Based on this required stirring time, the rotation time of stirring motor 62 in the forward direction (5 seconds) and the rotation time in the reverse direction (5 seconds) are determined. In FIG. 12, the required stirring time for liquid medications B and E that require stirring is the same and the required stirring time is fixed, however, the required stirring time may differ among types of liquid medications 5.

Figures 13, 14:
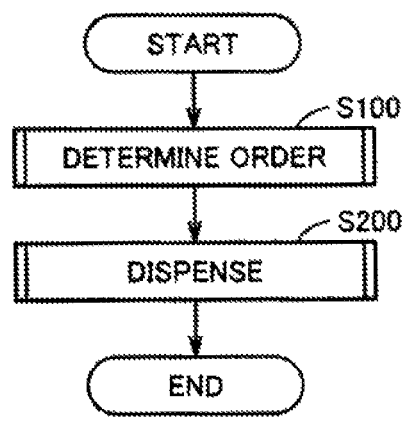
FIG. 13 shows an example of a prescription table indicating the types of liquid medications to be supplied to a prescription bottle.
FIG. 14 is a flowchart of liquid medication supply processing from a liquid medication bottle to a prescription bottle through the use of the liquid medication dispensing machine according to the present embodiment.

FIG. 13 shows an example of a prescription table indicating the types of liquid medications 5 to be supplied to prescription bottle 2. In the present example, three types of liquid medications 5 for a patient to take are mixed and supplied to prescription bottle 2 in accordance with a doctor's prescription. The prescription table stores data on the types of liquid medications and the dispensing quantity of liquid medications. In the present example, 20 ml of liquid medication B, 30 ml of liquid medication C and 40 ml of liquid medication G are supplied. Each piece of data in accordance with the prescription table may be input to control unit 90 by means of touch panel 14, or may be input to control unit 90 from an external computer via communication unit 92, as described above.

FIG. 14 is a flowchart of liquid medication supply processing from liquid medication bottle 23 to prescription bottle 2 through the use of liquid medication dispensing machine 1 according to the present embodiment. As shown in FIG. 14, in the liquid medication supply processing of this embodiment, the order of dispensing liquid medications 5 is determined first in step S100, and then actual dispensing is carried out in step S200. Throughout the present specification, a sequence in which respective liquid medications 5 contained in plurality of liquid medication bottles 23 are supplied successively and sequentially from liquid medication bottles 23 to prescription bottle 2 will be called a supply sequence. In this supply sequence, the order in which respective liquid medications 5 are supplied will be called a supply order.

Figure 15:
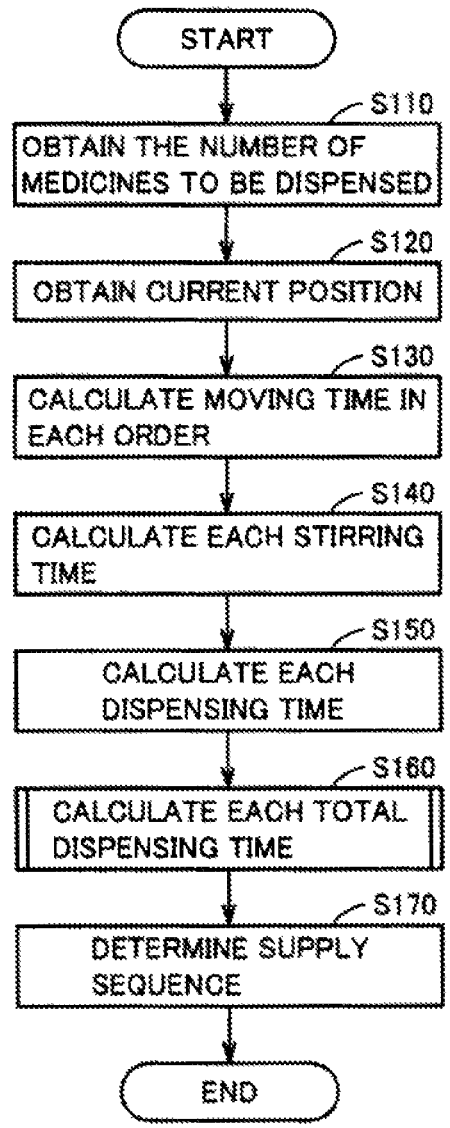
FIG. 15 is a flowchart showing the details of a step of determining the order shown in FIG. 14.

FIG. 15 is a flowchart indicating the details of step S100 of determining the order shown in FIG. 14. The supply sequence of plurality of liquid medications 5 and the supply order of respective liquid medications 5 are determined in accordance with steps which will be described below. First in step S110, the number of medicines to be dispensed to prescription bottle 2 is obtained. On this occasion, control unit 90 refers to the prescription table shown in FIG. 13 to recognize that three types of liquid medications of liquid medication B, liquid medication C, and liquid medication G are to be dispensed.

Then in step S120, the current position of liquid medication bottle 23 at the stage when the number of medicines to be dispensed is obtained. On this occasion, control unit 90 refers to the table shown in FIG. 11 in which the current position of each liquid medication bottle 23 is recorded based on the detection result obtained by bottle position detecting means 91 to recognize that a liquid medication currently located at the dispensing position is liquid medication A and the current positions of liquid medication bottles 23 containing three types of liquid medications B, C, and G to be dispensed. Then in step S130, based on the current positions of liquid medication bottles 23 obtained in step S120, control unit 90 calculates the moving time for each liquid medication bottle 23 to the dispensing position. In the present example, liquid medication A is located at the dispensing position. Thus, the moving time for liquid medication B to the dispensing position is 3 seconds, the moving time for liquid medication C to the dispensing position is 6 seconds, and the moving time for liquid medication G to the dispensing position is 6 seconds, as shown in FIG. 11.

Then in step S140, the stirring time for liquid medication 5 is calculated. Control unit 90 compares the prescription table shown in FIG. 13 and the table of liquid medications that require stirring shown in FIG. 12 to calculate that liquid medication B to be dispensed in the current dispensing processing is a liquid medication that requires stirring and that the required stirring time is 10 seconds.

Then in step S150, the dispensing time for each liquid medication is calculated. Control unit 90 refers to the prescription table of FIG. 13 to recognize the dispensing quantity of each of three types of liquid medications B, C and G and to calculate the dispensing time for each of liquid medications B, C and G based on the dispensing quantity of liquid medication 5 per unit time by pump driving motor 40. In the present example, pump driving motor 40 shall meet specifications that can transport 10 ml of liquid medication 5 for 1 second, and the dispensing time shall be proportional to the dispensing quantity of liquid medication 5. In this case, the dispensing time for liquid medication B is 2 seconds, the dispensing time for liquid medication C is 3 seconds, and the dispensing time for liquid medication G is 4 seconds.

Then in step S160, the total supply time required to supply all of three types of liquid medications B, C and G to prescription bottle 2 (hereinafter referred to as a TOTAL dispensing time) is calculated.

Figure 16:
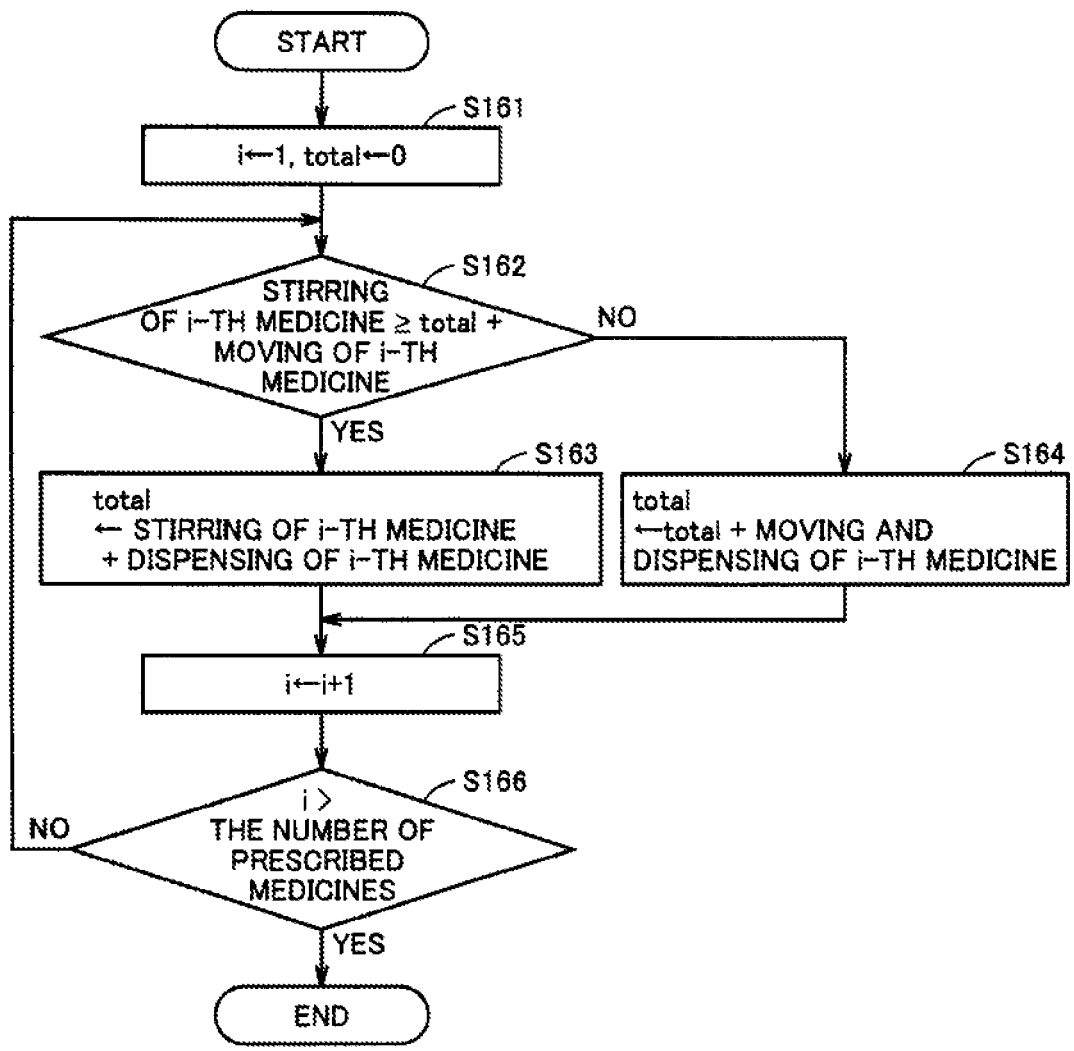
FIG. 16 is a flowchart showing the details of a step of calculating a TOTAL dispensing time.

FIG. 16 is a flowchart showing the details of step S160 of calculating the TOTAL dispensing time. Referring to FIG. 16, the method for calculating the TOTAL dispensing time will be described in detail. First, in step S161, a variable i is set at 1 and a variable total is set at 0.

Here, variable i indicates the number assigned to a liquid medication to be dispensed, and may have a value of an integer of 1 or more. For example, in accordance with the prescription table shown in FIG. 13, temporary numbering is carried out such that liquid medication B is numbered 1, liquid medication C is numbered 2, and liquid medication G is numbered 3. Variable total indicates time.

It should be noted that variable i does not indicate the supply order when actual dispensing is carried out in step S200. As will be described later, in order to determine the supply order when actual dispensing is carried out, the TOTAL dispensing times are calculated for all possible supply sequences, and then an optimal supply sequence (i.e., the supply sequence by which the TOTAL dispensing time becomes the shortest) is selected from among them. While liquid medication B is numbered 1, liquid medication C is numbered 2, and liquid medication G is numbered 3 in FIG. 13, these numbers are merely assigned in accordance with the order in which a doctor wrote the medications on the prescription, for example, or in the order in which data was input, for example. When determining the TOTAL dispensing time, arbitrary numbers of 1 to 3 are assigned to liquid medications B, C and G, and a total of six combinations of dispensing order are tried. Similarly, if two types of liquid medications are indicated in the prescription table, for example, a total of two combinations of dispensing order will be tried. If four types of liquid medications are indicated in the prescription table, for example, a total of twenty four combinations of dispensing order will be tried.

Returning to FIG. 16, then in step S162, the stirring time and the moving time for liquid medication B which is the first medicine are compared. Since variable total is 0 at this time point, only the stirring time and the moving time for liquid medication B need to be compared. In the present example, the required stirring time for liquid medication B is 10 seconds as shown in FIG. 12, and the moving time for moving liquid medication B to the dispensing position is 3 seconds as shown in FIG. 11. Thus, the stirring time is longer. That is, stirring of liquid medication B is not completed while liquid medication B is moved from the current position to the dispensing position, and the stirring time for liquid medication B will be rate-determining. Variable total is governed by the stirring time for liquid medication B. Therefore, the process proceeds into step S163, where variable total is set at the sum of the stirring time and the dispensing time for liquid medication B (10 seconds+2 seconds=12 seconds).

Since the time required until first liquid medication B is dispensed has been calculated in step S163, the process then proceeds into step S165, where variable i is incremented by 1. That is, the dispensing time for second liquid medication C will now be considered. In subsequent step S166, in order to determine whether the dispensing time for every prescribed medicine has been calculated, it is determined whether variable i has exceeded the number of prescribed medicines. In the present example, variable i at this time point is 2, and the number of prescribed medicines is 3. Since variable i is not more than the number of prescribed medicines, the process returns to step S162.

In a second round of step S162, the stirring time for liquid medication C, which is the second medicine, is compared with the sum of variable total at this time point and the moving time for liquid medication C. In the present example, liquid medication C does not require stirring. Thus, the stirring time is 0. That is, the sum of variable total at this time point and the moving time for liquid medication C is longer than the stirring time for liquid medication C. Therefore, the sum of variable total at this time point and the moving time for liquid medication C will be rate-determining, and the sum of variable total at this time point and the moving time for liquid medication C governs new variable total. Therefore, the process proceeds into step S164, where new variable total is set at the sum of variable total at this time point, the moving time for liquid medication C, and the dispensing time for liquid medication C.

FIG. 17 is a table indicating the current position of each liquid medication bottle 23 when liquid medication B is located at the dispensing position. Rotation drum 21 is rotationally moved so that the positions of liquid medication bottles 23 are changed from the positions in the table shown in FIG. 11, with the result that liquid medication B is currently located at the dispensing position. Therefore, the moving time required to move second liquid medication C to the dispensing position is 3 seconds as shown in FIG. 17. Therefore, the moving time and the dispensing time for liquid medication C (3 seconds+3 seconds=6 seconds) are added to variable total at this time point (12 seconds) to obtain new variable total of 18 seconds. The time required until second liquid medication C is dispensed is thereby calculated.

Then in step S165, variable i is incremented by 1, so that variable i is set at 3. Then in step S166, the value of variable i and the number of prescribed medicines are compared. Variable i and the number of prescribed medicines are both 3, and variable i is not more than the number of prescribed medicines. Thus, the process returns to step S162 again.

In a third round of step S162, the stirring time for liquid medication G, which is the third medicine, is compared with the sum of variable total at this time point and the moving time for liquid medication G. In the present example, liquid medication G does not require stirring. Thus, the stirring time is 0. Therefore, the process proceeds into step S164, where new variable total is set at the sum of variable total at this time point, the moving time for liquid medication G, and the dispensing time for liquid medication G.

FIG. 18 is a table showing the current position of each liquid medication bottle 23 when liquid medication C is located at the dispensing position. Rotation drum 21 is rotationally moved so that the positions of liquid medication bottles 23 are changed from the positions in the table shown in FIG. 17, with the result that liquid medication C is currently located at the dispensing position. Therefore, the moving time required to move third liquid medication G to the dispensing position is 12 seconds as shown in FIG. 18. Therefore, the moving time and the dispensing time for liquid medication C (12 seconds+4 seconds=16 seconds) are added to variable total at this time point (18 seconds) to obtain new variable total of 34 seconds. The time required until third liquid medication G is dispensed is thereby calculated.

Then in step S165, variable i is incremented by 1, so that variable i is set at 4. Then in step S166, the value of variable i and the number of prescribed medicines are compared. Variable i at this time point is 4, and the number of prescribed medicines is 3. Since variable i has exceeded the number of prescribed medicines, calculation of the TOTAL dispensing time is terminated.

Figures 19, 20:
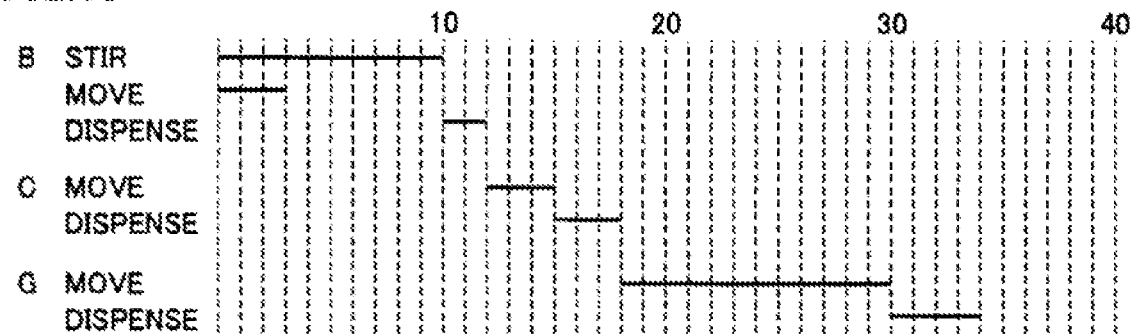
FIG. 19 is a timing chart showing the TOTAL dispensing time in the case of dispensing liquid medications B, C and G in this order.
FIG. 20 is a table showing the current position of each liquid medication bottle when liquid medication G is located at the dispensing position.

FIG. 19 is a timing chart showing the TOTAL dispensing time in the case of dispensing liquid medications B, C and G in this order. As described above, the stirring time for liquid medication B is longer than the moving time for liquid medication B. Thus, the TOTAL dispensing time in the case of dispensing liquid medications B, C and G in this order is calculated as 34 seconds by adding the time required to stir and dispense liquid medication B, the time required to move and dispense liquid medication C, and the time required to move and dispense liquid medication G.

In the present example, the number of medicines to be dispensed is 3. Therefore, a total of six combinations of dispensing order of liquid medications 5 to prescription bottle 2 by changing the order of liquid medications B, C and G are conceivable. For all these six combinations of dispensing order, the TOTAL dispensing time is calculated similarly to the foregoing.

For example, the TOTAL dispensing time in the case of dispensing liquid medications G, B and C in this order may be calculated next. In this case, referring to FIG. 16 again, since liquid medication G which is the first medicine does not require stirring before supply to prescription bottle 2, the time required until liquid medication G is dispensed is the sum of the moving time and the dispensing time for liquid medication G (6 seconds+4 seconds=10 seconds).

Liquid medication B, which is the second medicine, requires stirring for 10 seconds. Here, stirring of liquid medication B is carried out during the moving time for moving liquid medication G that does not require stirring to the dispensing position and the dispensing time for dispensing liquid medication G. Liquid medication bottle 23 containing liquid medication B is rotationally moved around drum axis line L1 while liquid medication B is being stirred.

Control unit 90 shown in FIG. 9 operates a liquid medication stirring unit to stir liquid medication B while liquid medication G is supplied to prescription bottle 2 and while rotation drum 21 as the bottle position changing unit is rotated to change the position of each liquid medication bottle 23. Control unit 90 stirs liquid medication B until the supply order of supplying liquid medication B to prescription bottle 2 comes in the supply sequence of supplying respective liquid medications 5 contained in plurality of liquid medication bottles 23 from liquid medication bottles 23 to prescription bottle 2, that is, until rotational movement of rotation drum 21 for moving liquid medication bottle 23 containing liquid medication B to the dispensing position is started. Control unit 90 starts supplying liquid medication B to prescription bottle 2 after supply of liquid medication G to prescription bottle 2 is completed. Control unit 90 stirs liquid medication B while liquid medication G whose supply order is earlier than liquid medication B is supplied to prescription bottle 2.

In the second round of step S162, the stirring time for liquid medication B is compared with the sum of variable total at this time point and the moving time for liquid medication B. FIG. 20 shows the table indicating the current position of each liquid medication bottle 23 when liquid medication G is located at the dispensing position. Referring to FIG. 20, the moving time required to move second liquid medication B to the dispensing position is 9 seconds as shown in FIG. 20. Variable total at this time point is the sum of the moving time and the dispensing time for liquid medication G which is the first medicine. That is, in the second round of step S162, control unit 90 compares a first liquid medication supply time required to supply liquid medication G and a second liquid medication stirring time required to stir liquid medication B.

Here, the first liquid medication supply time is the time required to supply liquid medication G which is the first liquid medication to be dispensed first from liquid medication bottle 23 as a first bottle containing liquid medication G, to prescription bottle 2. The second liquid medication stirring time is the time required to stir liquid medication B which is the second liquid medication to be dispensed secondarily. Control unit 90 compares a subtotal time obtained by adding the above-described first liquid medication supply time and a position changing time required for position changing of liquid medication bottle 23 with the above-described second liquid medication stirring time.

Comparing the stirring time for liquid medication B (10 seconds) and the sum of variable total at this time point and the moving time for liquid medication B (10 seconds+9 seconds=19 seconds), the latter is longer. Therefore, the process proceeds into step S164, where the moving time and the dispensing time for liquid medication B (9 seconds+2 seconds=11 seconds) are added to variable total at this time point (10 seconds) to obtain new variable total of 21 seconds. The time required until second liquid medication B is dispensed is thereby calculated.

Liquid medication C which is the third medicine does not require stirring. Thus, in step S164, new variable total is set at the sum of variable total at this time point, the moving time for liquid medication C, and the dispensing time for liquid medication C. Referring to FIG. 17, the moving time required to move third liquid medication C to the dispensing position is 3 seconds. Therefore, the moving time and the dispensing time for liquid medication C (3 seconds+3 seconds=6 seconds) are added to variable total at this time point (21 seconds) to obtain new variable total of 27 seconds. The time required until third liquid medication G is dispensed is thereby calculated.

Figure 21:
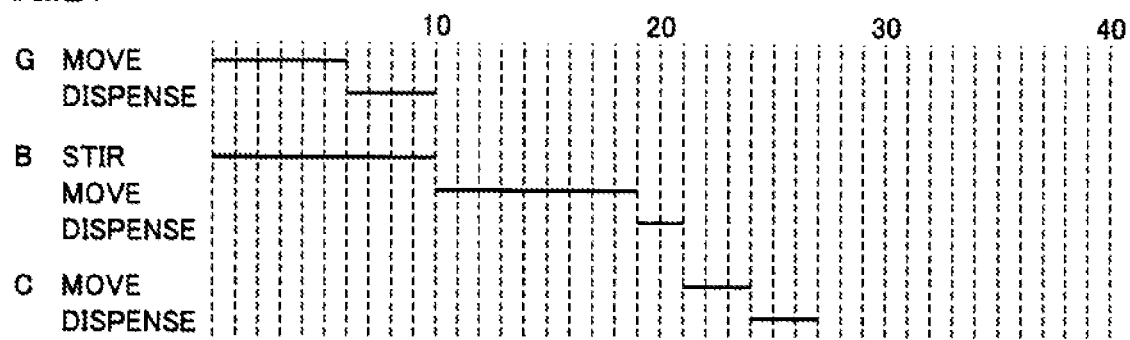
FIG. 21 is a timing chart showing the TOTAL dispensing time in the case of dispensing liquid medications G, B and C in this order.

FIG. 21 is a timing chart showing the TOTAL dispensing time in the case of dispensing liquid medications G, B and C in this order. The sum of the moving time and the dispensing time for first liquid medication G and the moving time for second liquid medication B is longer than the stirring time for liquid medication B, as described above. Therefore, the time required to move and dispense liquid medication G, the time required to move and dispense liquid medication B, and the time required to move and dispense liquid medication C are added to calculate that the TOTAL dispensing time in the case of dispensing liquid medications G, B and C in this order is 27 seconds.

Figure 22:
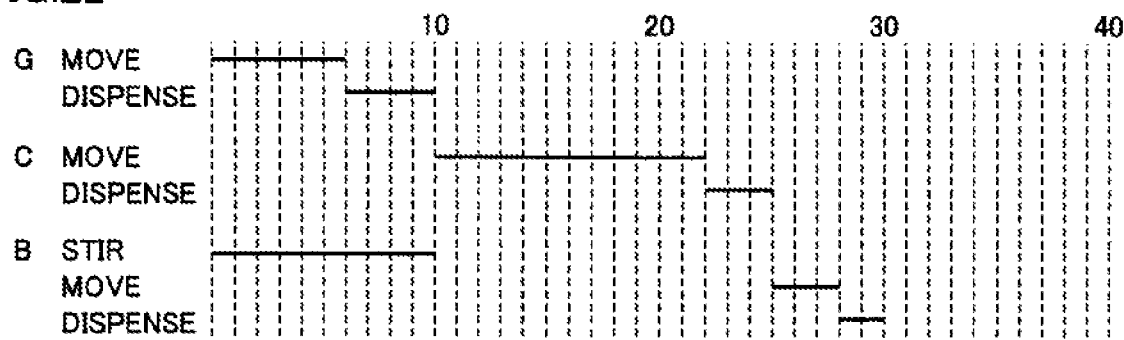
FIG. 22 is a timing chart showing the TOTAL dispensing time in the case of dispensing liquid medications G, C and B in this order.

FIG. 22 is a timing chart showing the TOTAL dispensing time in the case of dispensing liquid medications G, C and B in this order. Liquid medication B that requires stirring is dispensed thirdly. Stirring of liquid medication B is started at the same time when moving of first liquid medication G is started. Thus, stirring of liquid medication B will have been completed before dispensing of second liquid medication C is terminated. At an interval after termination of stirring of liquid medication B, control unit 90 starts supplying liquid medication B to prescription bottle 2. Therefore, the time required to move and dispense liquid medication G, the time required to move and dispense liquid medication C, and the time required to move and dispense liquid medication B are added to calculate that the TOTAL dispensing time in the case of dispensing liquid medications G, C and B in this order is 30 seconds.

Similarly, the TOTAL dispensing time is calculated for each of the case of dispensing liquid medication B, G, and C in this order, the case of dispensing liquid medication C, B, and G in this order, and the case of dispensing liquid medication C, G, and B in this order. That is, six TOTAL dispensing times, which are all the combinations of sequentially dispensing three types of liquid medications B, C and G, are calculated.

Returning to FIG. 15, then in step S170, the dispensing order when actually dispensing liquid medication 5 to prescription bottle 2 is determined based on the calculation result of the above-mentioned six TOTAL dispensing times. Specifically, among the six TOTAL dispensing times, the order in which the TOTAL dispensing time will be the shortest is selected, and that order is determined as the supply sequence in which respective liquid medications 5 contained in plurality of liquid medication bottles 23 are supplied from liquid medication bottles 23 to prescription bottle 2. In this way, the supply order in which respective liquid medications 5 (namely, liquid medications B, C and G) are supplied to prescription bottle 2 is determined, and step S100 shown in FIG. 14 is completed.

By minimizing the rotation of rotation drum 21, the time required to move liquid medication bottle 23 to the dispensing position can be minimized. Control unit 90 sets the supply sequence in which a plurality of types of liquid medications 5 contained in plurality of liquid medication bottles 23 are supplied to prescription bottle 2 such that the supply order of a stirring-requiring liquid medication comes after the supply order of a stirring-nonrequiring liquid medication. During the time required to stir the stirring-requiring liquid medication, the time that influences the TOTAL dispensing time can thereby be shortened. Therefore, the time required to dispense all the plurality of types of liquid medications can be shortened.

Figure 23:
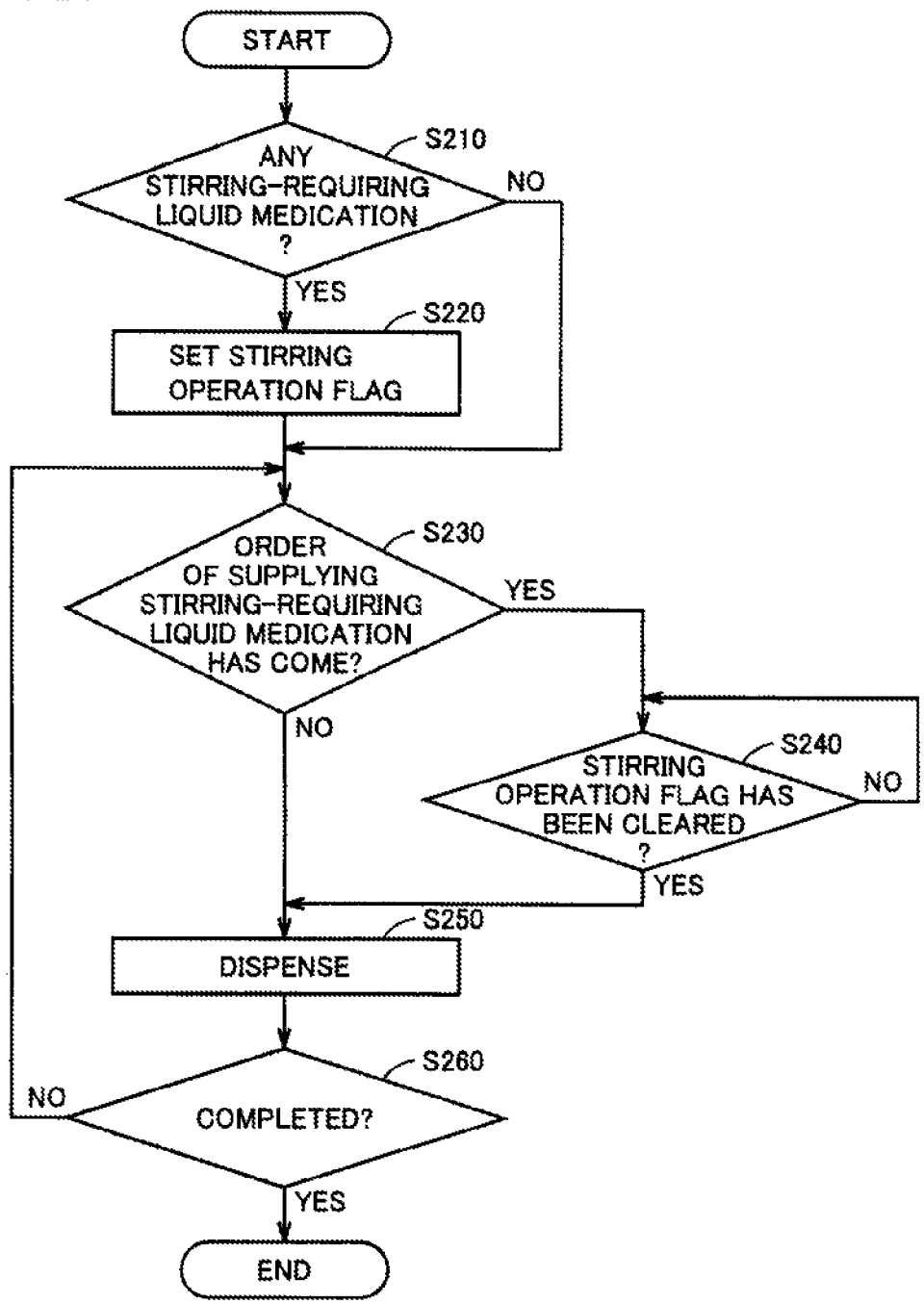
FIG. 23 is a flowchart showing the details of the step of dispensing a liquid medication shown in FIG. 14.

Then, liquid medication 5 is supplied from each of plurality of liquid medication bottles 23 containing liquid medications 5 to prescription bottle 2. FIG. 23 is a flowchart showing the details of step S200 of dispensing liquid medication 5 shown in FIG. 14. Referring to FIG. 23, in step S210, it is first determined whether plurality of liquid medications 5 to be supplied to prescription bottle 2 include a medicine that requires stirring. If there is a stirring-requiring liquid medication, the process proceeds into step S220, where a stirring operation flag is set. Then the process proceeds into step S230. If there is no medicine that requires stirring, the process directly proceeds into step S230, skipping step S220.

Figure 24:
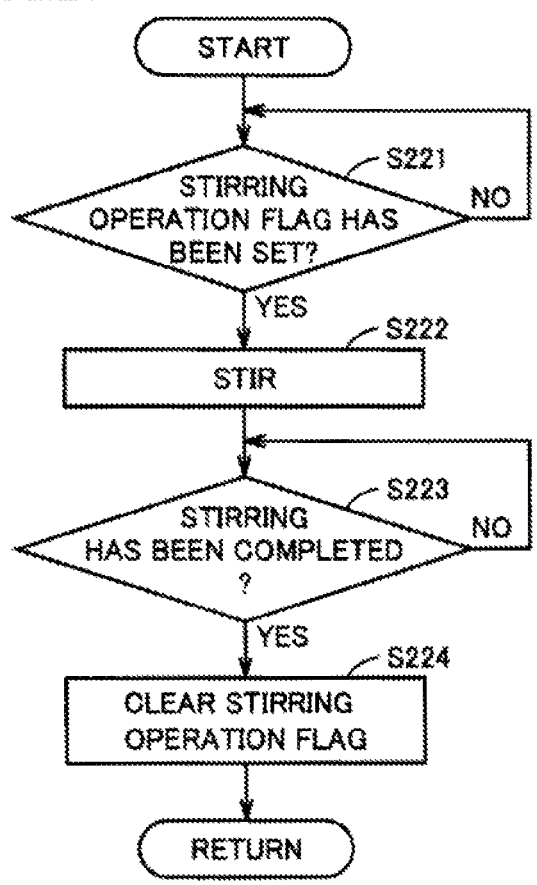
FIG. 24 is a flowchart showing a subroutine of stirring a liquid medication.

FIG. 24 is a flowchart showing a subroutine of stirring liquid medication 5. The subroutine shown in FIG. 24 starts simultaneously with startup of liquid medication dispensing machine 1 and is always executed. As shown in step S221, whether or not the stirring operation flag has been set is always monitored. While the stirring operation flag is not set, the subroutine is in a standby state waiting for an instruction.

When the stirring operation flag is set in step S220 shown in FIG. 23, it is determined in step S221 that the stirring operation flag has been set, and the process proceeds into step S222. In step S222, control unit 90 drives motor 62 for stirring liquid medication 5, thereby rotating liquid medication bottle 23. By rotating liquid medication bottle 23 both in forward and reverse directions, a turbulent flow is produced in liquid medication bottle 23, thereby stirring liquid medication 5 in liquid medication bottle 23. Stirring is continued until it is determined in step S223 that stirring has been completed. A determination about completion of stirring is made by, for example, detecting with a timer whether or not the driving time of motor 62 has exceeded a predetermined time.

When the stirring operation flag is set in step S220, a determination made in step S221 is YES. Then, the process proceeds into step S222, where stirring is started. When a prescription includes a plurality of liquid medications 5 that require stirring, stirring operation flags for plurality of liquid medications 5 are set simultaneously, and stirring of plurality of liquid medications 5 is started all at once.

When it is determined that stirring has been completed, motor 62 is suspended. Then, the process proceeds into step S224, where the stirring operation flag is cleared. The subroutine of FIG. 24 is then returned to return to the standby state.

It is noted that the subroutine shown in FIG. 24 may always be executed simultaneously with device startup, as described above. However, a subroutine start flag may be set after the supply sequence of liquid medications 5 is determined. In this case, the subroutine may be terminated after all of required plurality of types of liquid medications 5 are supplied to prescription bottle 2.

Returning to FIG. 23, it is then determined in step S230 whether or not the dispensing order of a medicine that requires stirring has come. If the supply order of the stirring-requiring liquid medication has come, it is then determined in step S240 whether the stirring operation flag has been cleared. That is, when the supply order of the stirring-requiring liquid medication has come, it is determined whether stirring of liquid medication 5 has already been carried out in accordance with the subroutine shown in FIG. 24 and as a result, whether the stirring operation flag has been cleared in step S224. If the stirring operation flag has not been cleared, stirring has not been terminated. Thus, the process waits until stirring is completed and the stirring operation flag is cleared. If it is determined that the stirring operation flag has been cleared, the process proceeds into step S250.

If the supply order of a stirring-nonrequiring liquid medication that does not require stirring has come, dispensing of liquid medication 5 is possible regardless of the stirring operation flag. Thus, the process directly proceeds into step S250 from step S230. Then in step S250, liquid medication bottle 23 containing liquid medication 5 to be dispensed is moved to the dispensing position, and then liquid medication 5 is dispensed from liquid medication bottle 23 to prescription bottle 2.

Here, when the stirring operation flag is set in step S220, stirring is immediately started in step S222. If liquid medication 5 to be supplied first to prescription bottle 2 after the stirring operation flag is set in step S220 is a stirring-nonrequiring liquid medication that does not require stirring before supply to prescription bottle 2, movement of liquid medication bottle 23 is immediately started in step S250. Control unit 90 operates rotationally driving unit 61 constituting the liquid medication stirring unit to stir liquid medication 5 in liquid medication bottle 23 while rotation drum 21 changes the position of liquid medication bottles 23.

Then, the process proceeds into step S260, where it is determined whether or not all of target liquid medications 5 indicated on a prescription have been supplied to prescription bottle 2. If the supply has not been completed, the process returns to step S230. If all of liquid medications 5 have been dispensed, supply of liquid medications 5 to prescription bottle 2 is completed, and step S200 shown in FIG. 14 is completed.

As described above, in liquid medication dispensing machine 1 of the present embodiment, liquid medication 5 that requires stirring before supply to prescription bottle 2 is stirred while another liquid medication 5 is supplied to prescription bottle 2 and/or while liquid medication bottles 23 are changed in position. By causing the stirring time for a stirring-requiring liquid medication to overlap the dispensing time and/or the moving time for another liquid medication 5, the time for carrying out stirring alone can be shortened, and typically, the time for carrying out stirring alone can be eliminated. Therefore, the dispensing time for liquid medication 5 can be shortened.

It is noted that the supply sequence in which plurality of types of liquid medications 5 contained in plurality of liquid medication bottles 23 are supplied to prescription bottle 2 may be set such that the supply order of liquid medication B which is a stirring-requiring liquid medication comes after the supply order of liquid medication G which is a stirring-nonrequiring liquid medication. Alternatively, the supply sequence may be set previously in accordance with the order in which a doctor wrote the prescription, for example. Control unit 90 does not need to change the supply sequence. Even if the supply sequence has been set previously and the first supply order has been assigned to liquid medication B that requires stirring, the time for carrying out only stirring of liquid medication B can be shortened by causing the stirring time and the moving time for liquid medication B to overlap, as shown in FIG. 19. Therefore, the dispensing time for liquid medication 5 can be shortened.

Second Embodiment

Figure 25:
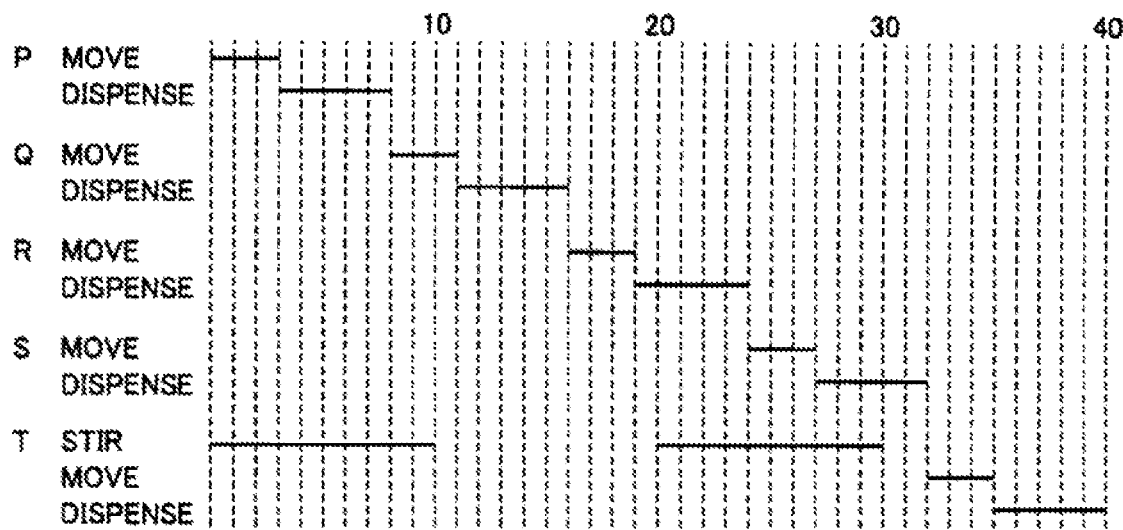
FIG. 25 is a timing chart showing the TOTAL dispensing time according to a second embodiment.

FIG. 25 is a timing chart showing the TOTAL dispensing time according to a second embodiment. The second embodiment will describe an example of supplying liquid medications 5 to prescription bottle 2 in accordance with a prescription of supplying 50 ml of each of five types of liquid medications P, Q, R, S, and T. The dispensing time for each of liquid medications P, Q, R, S, and T shall be 5 seconds equally. At this time, liquid medication bottles 23 containing five types of liquid medications P, Q, R, S, and T, respectively, are arranged on liquid medication bottle holder 32 adjacently to one another. Thus, the moving time for each liquid medication bottle 23 to the dispensing position shall be 3 seconds.

Among five types of liquid medications P, Q, R, S, and T, only liquid medication T shall be a stirring-requiring liquid medication that requires stirring before supply to prescription bottle 2, and other liquid medications P, Q, R, and S shall be stirring-nonrequiring liquid medications that do not require stirring before supply to prescription bottle 2.

As described with reference to FIG. 23, the stirring operation flag is set at the start of supply of liquid medication 5 to prescription bottle 2. Thus, as shown in FIG. 25, stirring of liquid medication T is started simultaneously with the start of moving liquid medication P. Liquid medication T is stirred for 10 seconds, and then stirring is interrupted.

After the interruption of a predetermined time (in the present example, 10 seconds), liquid medication T is stirred again for 10 seconds.

In this way, if liquid medication T which is a stirring-requiring liquid medication is repeatedly stirred before supply to prescription bottle 2, liquid medication T can be stirred in a time zone closer to the time point when the supply order of liquid medication T comes, namely, the time point when movement of liquid medication bottle 23 containing liquid medication T to the dispensing position is started. Therefore, a suspended component contained in liquid medication T can be prevented more reliably from precipitating to the bottom of liquid medication bottle 23. Thus, liquid medication T in more uniform state can be supplied to prescription bottle 2.

Third Embodiment

Figure 26:
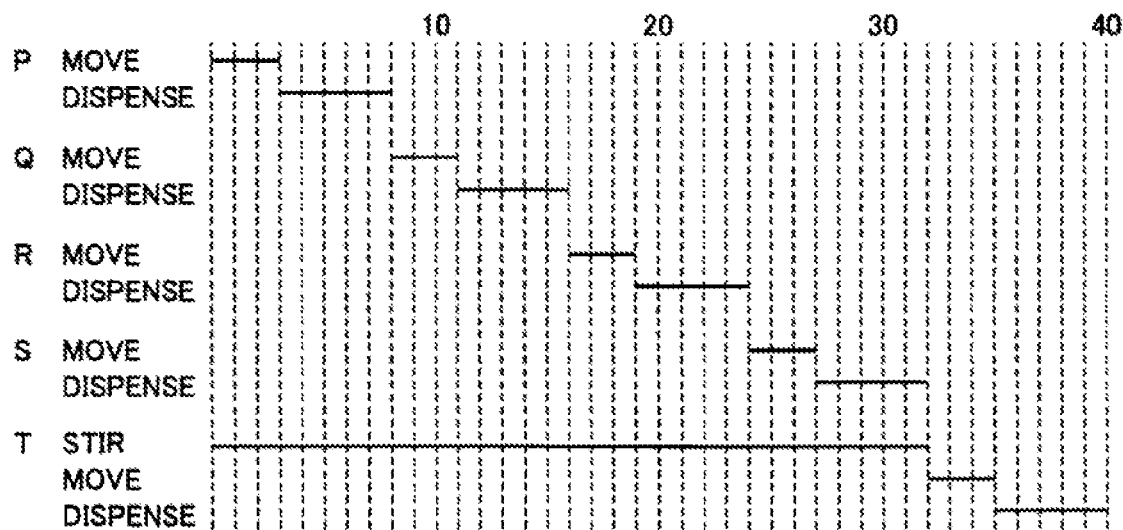
FIG. 26 is a timing chart showing the TOTAL dispensing time according to a third embodiment.

FIG. 26 is a timing chart showing the TOTAL dispensing time according to a third embodiment. The third embodiment is an example of supplying five types of liquid medications P, Q, R, S, and T similar to those of the second embodiment described above to prescription bottle 2. In the third embodiment, stirring of liquid medication T is continued from the start of moving liquid medication P to the end of dispensing liquid medication S, that is, until the supply order of liquid medication T comes, as shown in FIG. 26.

According to the dispensing processing shown in the third embodiment, similarly to the second embodiment, liquid medication T can be stirred in a time zone closer to the time point when the supply to prescription bottle 2 is started, and a suspended component contained in liquid medication T can be prevented more reliably from precipitating to the bottom of liquid medication bottle 23. Thus, liquid medication T in more uniform state can be supplied to prescription bottle 2.

Fourth Embodiment

Figure 27:
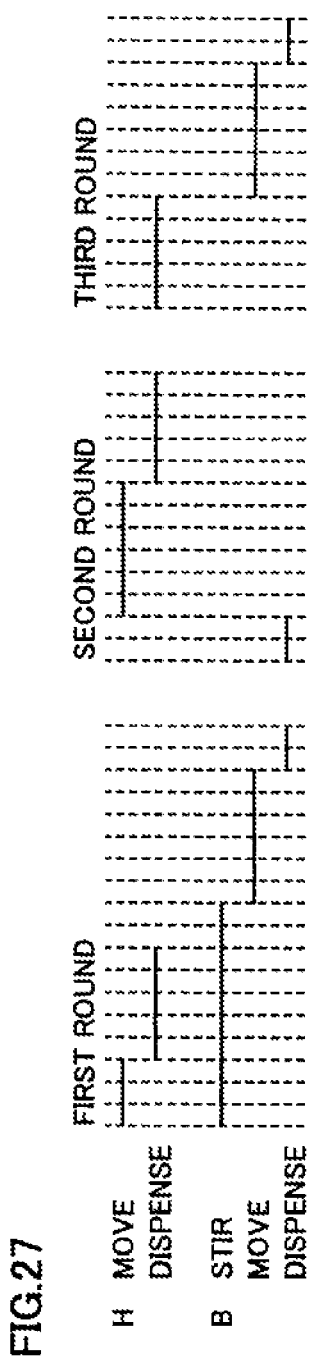
FIG. 27 is a timing chart showing the TOTAL dispensing time according to a fourth embodiment.

FIG. 27 is a timing chart showing the TOTAL dispensing time according to a fourth embodiment. The fourth embodiment will describe an example of supplying liquid medications 5 to prescription bottle 2 in accordance with a prescription in which two types of liquid medications B and H arranged as indicated in the table shown in FIG. 11 are supplied, the dispensing quantity of liquid medication B being 20 ml and the dispensing quantity of liquid medication H being 50 ml. The dispensing time for liquid medication B shall be 2 seconds, and the dispensing time for liquid medication H shall be 5 seconds. As shown in FIG. 12, liquid medication B shall be a stirring-requiring liquid medication, and liquid medication H shall be a stirring-nonrequiring liquid medication. Moreover, as shown in FIG. 27, three rounds of prescription of supplying liquid medications B and H shall be performed successively.

In this case, liquid medication B that requires stirring before supply to prescription bottle 2 should only be stirred in the first round in the three successive rounds of prescription. After a short time since liquid medication B is stirred in the first round of prescription, liquid medication B is dispensed in accordance with the second and third rounds of prescription. In the second and third rounds of prescription, not long time has elapsed since liquid medication B is stirred in the first round of prescription, and it is considered that liquid medication B has already been stirred. Liquid medication B is a stirring-requiring liquid medication in the first round of prescription, but can be treated as a stirring-nonrequiring liquid medication in the second and third rounds of prescription. Therefore, liquid medication B does not require stirring again in the second and third rounds of prescription, and the required time can be shortened because of the stirring time for liquid medication B.

In this way, the TOTAL dispensing time for liquid medications B and H in the second and third rounds of prescription can be shortened. In the second and third rounds of prescription, control unit 90 starts supplying liquid medication B to prescription bottle 2 at an interval after the end of stirring of liquid medication B. Such dispensing processing is particularly effective for shortening the TOTAL dispensing time if all of liquid medications included in a prescription are stirring-requiring liquid medications.

Fifth Embodiment

Figure 28:
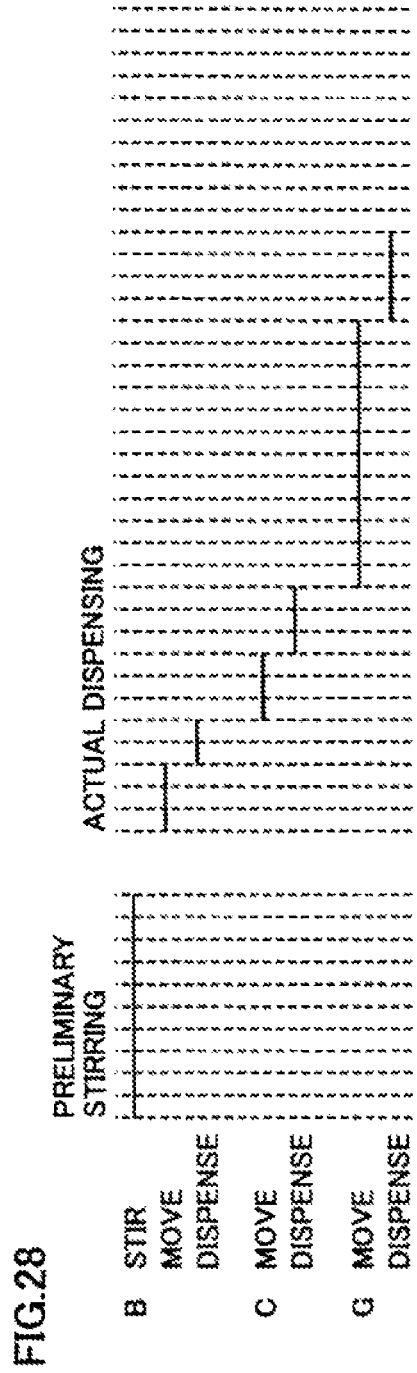
FIG. 28 is a timing chart showing the TOTAL dispensing time according to a fifth embodiment.

FIG. 28 is a timing chart showing the TOTAL dispensing time according to a fifth embodiment. The fifth embodiment is an example of supplying three types of liquid medications B, C and G similar to those of the first embodiment described above to prescription bottle 2. Depending on the type of stirring-requiring liquid medication, liquid medication 5 can be maintained homogeneously for a long time (e.g., 10 hours or more) after stirring. Such a liquid medication should only be stirred once a day, for example, only at the time of startup of liquid medication dispensing machine 1 during the day. Then, stirring is unnecessary at the time of subsequent actual dispensing. In the fifth embodiment, liquid medication B shall be a liquid medication of the type that can maintain sufficient homogeneity by stirring once a day.

Therefore, by stirring liquid medication B previously as shown in FIG. 28, liquid medication B can be treated as a stirring-nonrequiring liquid medication that does not require stirring before supply to prescription bottle 2 at the time of actual dispensing. Thus, the TOTAL required time can be shortened because of the stirring time for liquid medication B. Control unit 90 starts supplying liquid medication B to prescription bottle 2 at an interval after the end of stirring of liquid medication B. Then, the TOTAL dispensing time in the case of dispensing liquid medications B, C and G in this order can be significantly shortened as compared to FIG. 19.

It is noted that, in the embodiments described above, the TOTAL dispensing time is calculated in consideration of the moving time of moving liquid medication bottle 23 to the dispensing position in the structure where medication bottle 23 is movable within liquid medication dispensing machine 1. In the structure where liquid medication bottle 23 is not moved within liquid medication dispensing machine 1, the TOTAL dispensing time may be calculated without taking into consideration the moving time for liquid medication bottle 23. That is, the TOTAL dispensing time may be calculated by adding the dispensing time and the stirring time for plurality of liquid medications 5 as appropriate.

Although the embodiments of the present invention have been described above, the structures of the respective embodiments may be combined as appropriate. It should be understood that the embodiments disclosed herein are illustrative and non-restrictive in every respect. The scope of the present invention is defined by the claims not by the description above, and is intended to include any modification within the meaning and scope equivalent to the terms of the claims.

REFERENCE SIGNS LIST

1 liquid medication dispensing machine; 2 prescription bottle; 3 liquid medication supply unit; 5 liquid medication;

14 touch panel; 17 output unit; 17a, 17b printer; 21 rotation drum; 22 drum rotating motor; 23 liquid medication bottle; 32 liquid medication bottle holder; 39 moving motor; 40 pump driving motor; 45 electronic balance; 50 elevating device; 61 rotationally driving unit; 62 motor; 90 control unit; 91 bottle position detecting means; 92 communication unit; 93 memory; 94 recording medium access unit.

The invention claimed is:

1. A method of controlling a liquid medication dispensing machine supplying a liquid medication to a prescription bottle in accordance with a prescription information, said prescription information including a first liquid medication not requiring stirring before supply to said prescription bottle and a second liquid medication requiring stirring before supply to said prescription bottle, comprising the steps of:

setting a supply sequence such that a supply order of said second liquid medication comes after a supply order of said first liquid medication:

stirring said second liquid medication while said first liquid medication is supplied from a first bottle containing said first liquid medication to said prescription bottle;

supplying said second liquid medication from a second bottle containing said second liquid medication to said prescription bottle after supply of said first liquid medication to said prescription bottle is completed; and a step of changing positions of said first bottle and said second bottle, wherein said second liquid medication is stirred while the positions of said first bottle and said second bottle are changed.

2. A method of controlling a liquid medication dispensing machine comprising steps of:

supplying a plurality of liquid medications from a plurality of liquid medication bottles containing said plurality of liquid medications to a prescription bottle, respectively, said plurality of liquid medications including a stirring-requiring liquid medication that requires stirring before supply to said prescription bottle;

stirring said stirring-required liquid medication by a time when a supply order of supplying said stirring-requiring liquid medication to said prescription bottle comes in a supply sequence in which said plurality of liquid medications contained in said plurality of liquid medication bottles are supplied from said plurality of liquid medication bottles to said prescription bottle, respectively, said stirring-requiring liquid medication being stirred while the liquid medication having said supply order earlier than said stirring-requiring liquid medication is supplied to said prescription bottle; and stirring said stirring-required liquid medication while the positions of said plurality of liquid medications are changed.

3. The method of controlling a liquid medication dispensing machine according to claim 2, wherein said plurality of liquid medications include a stirring-nonrequiring liquid medication that does not require stirring before supply to said prescription bottle, and said supply order of said stirring-requiring liquid medication in said supply sequence comes after said supply order of said stirring-nonrequiring liquid medication in said supply sequence.

4. A method of controlling a liquid medication dispensing machine supplying a liquid medication to a prescription bottle in accordance with a prescription information, comprising steps of:

supplying a first liquid medication from a first bottle containing said first liquid medication to said prescription bottle, said first liquid medication not requiring stirring before supply to said prescription bottle;

supplying a second liquid medication from a second bottle containing said second liquid medication to said prescription bottle, said second liquid medication requiring stirring before supply to said prescription bottle;

setting a supply sequence in accordance with said prescription information such that a supply order of said second liquid medication comes after a supply order of said first liquid medication when said prescription information includes said first liquid medication and said second medication; and stirring said second liquid medication while said first liquid medication is supplied; and a step of changing positions of said first bottle and said second bottle, wherein said second liquid medication is stirred while the positions of said first bottle and said second bottle are changed.

* * * * *